United States Patent
Shiotani et al.

(10) Patent No.: US 12,372,774 B2
(45) Date of Patent: Jul. 29, 2025

(54) ENDOSCOPE IMAGING UNIT AND ENDOSCOPE

(71) Applicant: OLYMPUS CORPORATION, Hachioji (JP)

(72) Inventors: Koichi Shiotani, Hachioji (JP); Takahiko Mitani, Hachioji (JP); Yuki Nakayama, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 18/243,471

(22) Filed: Sep. 7, 2023

(65) Prior Publication Data
US 2023/0418045 A1  Dec. 28, 2023

Related U.S. Application Data

(63) Continuation of application No. PCT/JP2021/009487, filed on Mar. 10, 2021.

(51) Int. Cl.
*G02B 7/04* (2021.01)
*G02B 23/24* (2006.01)

(52) U.S. Cl.
CPC ....... *G02B 23/2484* (2013.01); *G02B 23/243* (2013.01)

(58) Field of Classification Search
CPC ... A61B 1/00096; A61B 1/04; A61B 1/00188; A61B 1/042; A61B 1/05; A61B 1/00009; A61B 1/0676; A61B 1/00071; A61B 1/00128; A61B 1/0011; A61B 1/00195; G02B 27/62; G02B 7/025; G02B 23/2476;
(Continued)

(56) References Cited

U.S. PATENT DOCUMENTS

| | | |
|---|---|---|
| 2002/0128535 A1 | 9/2002 | Kikuchi et al. |
| 2013/0027534 A1 | 1/2013 | Kibayashi |
| 2017/0296044 A1* | 10/2017 | Wataya ................. H04N 23/55 |

FOREIGN PATENT DOCUMENTS

| | | |
|---|---|---|
| JP | 11-47077 A | 2/1999 |
| JP | 2002-336190 A | 11/2002 |
| JP | 2018-81270 A | 5/2018 |

(Continued)

OTHER PUBLICATIONS

International Search Report dated May 25, 2021, issued in counterpart International Application No. PCT/JP2021/009487, with English Translation. (4 pages).

*Primary Examiner* — Masum Billah
(74) *Attorney, Agent, or Firm* — WHDA, LLP; Tsuyoshi Nakamura

(57) ABSTRACT

An endoscope imaging unit includes: an objective lens including a first lens and a second lens; an imaging element configured to capture an image formed by the objective lens; a first lens frame configured to hold the first lens, the first lens frame including a lens barrel that holds the first lens and a flange portion that extends outward from an outer peripheral portion of the lens barrel; a second lens frame that is fixed to the first lens frame and holds the second lens; and a holder that accommodates at least part of the first lens frame and the second lens frame therein and holds the outer peripheral surface of the flange portion of the first lens frame; wherein the flange portion is fixed to the holder on a side surface thereof in an extending direction.

5 Claims, 14 Drawing Sheets

(58) Field of Classification Search
CPC ... G02B 23/2453; G02B 23/2484; G02B 7/04
USPC .......................................................... 348/76
See application file for complete search history.

(56) References Cited

FOREIGN PATENT DOCUMENTS

| | | | |
|---|---|---|---|
| JP | 2020-130437 A | 8/2020 | |
| JP | 2020-201408 A | 12/2020 | |
| WO | 2012/137739 A1 | 10/2012 | |
| WO | 2017/022279 A1 | 2/2017 | |
| WO | WO-2021073619 A1 * | 4/2021 | ........... A61B 1/0011 |

* cited by examiner

ENDOSCOPE IMAGING UNIT AND ENDOSCOPE

CROSS-REFERENCE TO RELATED APPLICATIONS

The present application is a continuation application based on PCT Patent Application No. PCT/JP2021/009487, filed on Mar. 10, 2021, the entire contents of which is hereby incorporated by reference.

BACKGROUND

Technical Field

The present invention relates to an endoscope imaging unit and an endoscope.

Description of the Background

An imaging unit including an objective lens having a plurality of lenses and an imaging element is arranged at the distal end of the endoscope. Demands for miniaturization and improvement in optical performance of endoscopes are increasing. In an imaging unit of an endoscope, it is required to arrange a plurality of lenses with high precision.

In a configuration in which multiple lenses in an objective lens are fixed to a single lens frame, it is necessary to improve the processing accuracy of the lens frame. On the other hand, it is known to relax the processing accuracy of each lens frame by dividing and fixing a plurality of lenses into a plurality of lens frames and then connecting the plurality of lens frames to each other to manufacture an imaging unit.

For example, the optical device described in Japanese Unexamined Patent Applications, First Publication No. 2018-81270 (hereinafter referred to as Patent Document 1) a first front group lens, a second front group lens, and a rear group lens by dividing them into a first front group holding frame, a second front group holding frame, and a rear group holding frame, respectively. The first front group holding frame to which the lens is fixed, the second front group holding frame, and the rear group holding frame are adhered and fixed to each other.

For example, in the imaging unit described in PCT International Publication No. WO 2017/022279 (hereinafter referred to as Patent Document 2), a front group lens and a rear group lens are held by a front group lens frame and a rear group lens frame, respectively. The front lens group frame and the rear lens group frame are bonded and fixed to each other while their relative positions in the radial direction are adjusted.

For example, as in Patent Documents 1 and 2, when the lenses used in the imaging unit are held by a plurality of lens frames and the plurality of lens frames are adhered to each other, the plurality of lens frames constitute a holder having a cylindrical shape as a whole.

A cylindrical holder is placed on the outermost part of the imaging unit, and it is attached to a device body such as an endoscope. Therefore, if the holder is deformed by heat, external force, or the like, the lens frames may be displaced relative to each other, or excessive stress may be applied to the bonding portion, resulting in damage to the bonding portion. The same applies when an impact force acts on the holder.

SUMMARY

The present invention provides an endoscope imaging unit and an endoscope that can easily maintain optical performance even when a load is applied to a holder arranged radially outside the objective lens.

An endoscope imaging unit used by being installed at a distal end of an endoscope, includes: an objective lens including a first lens and a second lens; an imaging element configured to capture an image formed by the objective lens; a first lens frame configured to hold the first lens, the first lens frame including a lens barrel that holds the first lens and a flange portion that extends outward from an outer peripheral portion of the lens barrel; a second lens frame that is fixed to the first lens frame and holds the second lens; and a holder that accommodates at least part of the first lens frame and the second lens frame therein and holds the outer peripheral surface of the flange portion of the first lens frame, wherein the flange portion is fixed to the holder on a side surface thereof in an extending direction, and the second lens frame is fixed to an image-side or an object-side end face of the flange portion of the first lens frame without contacting the imaging element and the holder and with a gap between the imaging element and the holder.

An endoscope according to a second aspect includes the endoscope imaging unit according to the first aspect.

According to the first and second aspects, it is possible to provide an endoscope imaging unit and an endoscope that can easily maintain optical performance even when a load is applied to the holder arranged radially outside the objective lens.

EMBODIMENTS

Figure 1:
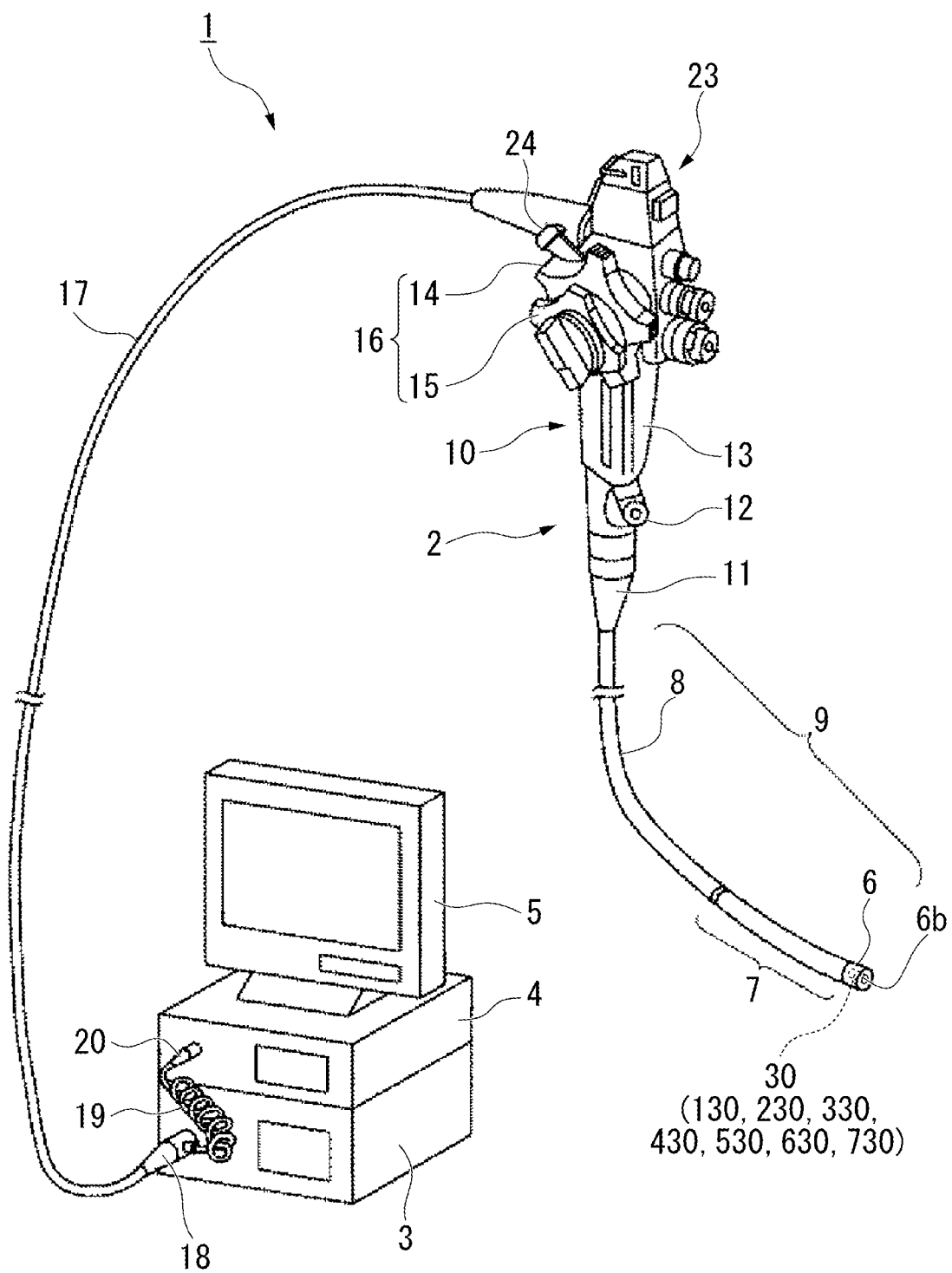
FIG. 1 is a schematic perspective view showing an example of an endoscope according to a first embodiment of the present invention.

Embodiments of the present invention will be described below with reference to the accompanying drawings. In all the drawings, even when the embodiments are different, the same or corresponding members are denoted by the same reference numerals, and common explanations are omitted.

First Embodiment

An endoscope according to the first embodiment of the present invention will be described.

FIG. 1 is a schematic perspective view showing an example of an endoscope according to the first embodiment of the invention.

The endoscope system 1 shown in FIG. 1 has an endoscope 2 according to this embodiment, a light source device 3, a video processor 4, and a color monitor 5.

The application of the endoscope 2 is not particularly limited. For example, the endoscope 2 may be a medical endoscope or an industrial endoscope.

The endoscope 2 has an insertion portion 9 inserted into the subject, an operating portion 10 arranged outside the subject, and a universal cord 17 extending from the operating portion 10. Inside the universal cord 17, a light guide bundle, which will be described later, and an electric cable forming an electric signal transmission path are inserted along the longitudinal direction. A scope connector 18 is provided at the distal end of the universal cord 17 to optically couple the illumination light from the light source device 3 that supplies illumination light to the incident end of the light bundle.

The electric cable in the universal cord 17 extends inside the scope cable 19 branched from the scope connector 18. An electrical connector portion 20 for electrically connecting the end of the electrical cable in the scope cable 19 to the video processor 4 is provided at the end in the extending direction of the scope cable 19. When the electrical connector portion 20 is connected to the video processor 4, electrical components built in the endoscope 2 and the video processor 4 are communicably connected through an electrical cable.

The insertion portion 9 has a distal end portion 6, a bending portion 7, and a flexible tube portion 8 in this order from the distal end, which is the distal end in the direction of insertion into the subject, toward the proximal end connected to the operation portion 10.

A well-known distal end opening, an observation window, and an illumination window are formed on the distal end surface of the distal end portion 6. However, in the example shown in FIG. 1, only the observation window 6b is shown for ease of viewing.

An imaging unit 30 for imaging the subject in front of the distal end portion 6 is arranged inside the distal end portion 6 at a position facing the observation window 6b. A detailed configuration of the imaging unit 30 will be described later.

The distal end of the light guide bundle that transmits the illumination light is arranged on the back side of the illumination window. The light guide bundle is inserted inside the insertion portion 9, passes through the inside of the operation portion 10, and extends inside the universal cord 17. The proximal end of the light guide bundle is located inside scope connector 18. When the scope connector 18 is connected to the light source device 3, illumination light from the light source device 3 is optically coupled to the proximal end of the light guide bundle. As a result, the illumination light generated by the light source device 3 is optically transmitted to the illumination window in the distal end portion 6, and the illumination light is emitted to the outside of the distal end portion 6.

The bending portion 7 is connected to the proximal end of the distal end portion 6. The bending portion 7 is a bendable tubular portion. The bending amount of the bending portion 7 is changed by operating the operation portion 10. The orientation of the distal end portion 6 is changed according to the amount of bending and the direction of bending of the bending portion 7.

The bending portion 7 includes, for example, a plurality of node rings. A node ring is rotatably connected to an adjacent node ring. In the bending portion 7, two systems of operation wires including a first operation wire and a second operation wire, a ride guide bundle, an electric cable, a treatment instrument channel, which will be described later, and the like are inserted inside the node ring. Each operation wire extends from the bending portion 7 through the inside of the flexible tube portion 8 to the operation portion 10.

The operation portion 10 has an operation portion main body 13 that is held by the operator, and is used for various operations on the endoscope 2.

For example, a bending operation portion 16, a switch portion 23, and an operation lever 24 are provided on the upper portion of the operation portion main body 13.

The bending operation portion 16 has operation knobs 14 and 15 for operating the bending amount and bending direction of the bending portion 7. For example, the operating knobs 14 and 15 can independently pull the first operating wire and the second operating wire, respectively. When the operation knobs 14 and 15 are rotated appropriately, the bending portion 7 is bent according to the amount and direction of rotation of each.

The switch portion 23 has at least one switch that is mainly used for operating the imaging function.

For example, when the imaging unit 30 described later has a focus adjustment function, a magnification adjustment function, and a zoom variable function, the operation lever 24 is used to operate each adjustment amount and change amount.

A forceps port 12 and an anti-break portion 11 are provided at the bottom of the operation portion main body 13.

The forceps port 12 is an opening that communicates with the proximal end of the treatment instrument channel that extends from the interior of the operating portion 10 through the insertion portion 9 to the distal end opening of the distal end portion 6.

The folding stopper 11 connects the proximal end of the insertion portion 9 and the operation portion 10.

Next, an example of the imaging unit 30 (endoscope imaging unit) of the present embodiment arranged inside the distal end portion 6 will be described.

Figure 2:
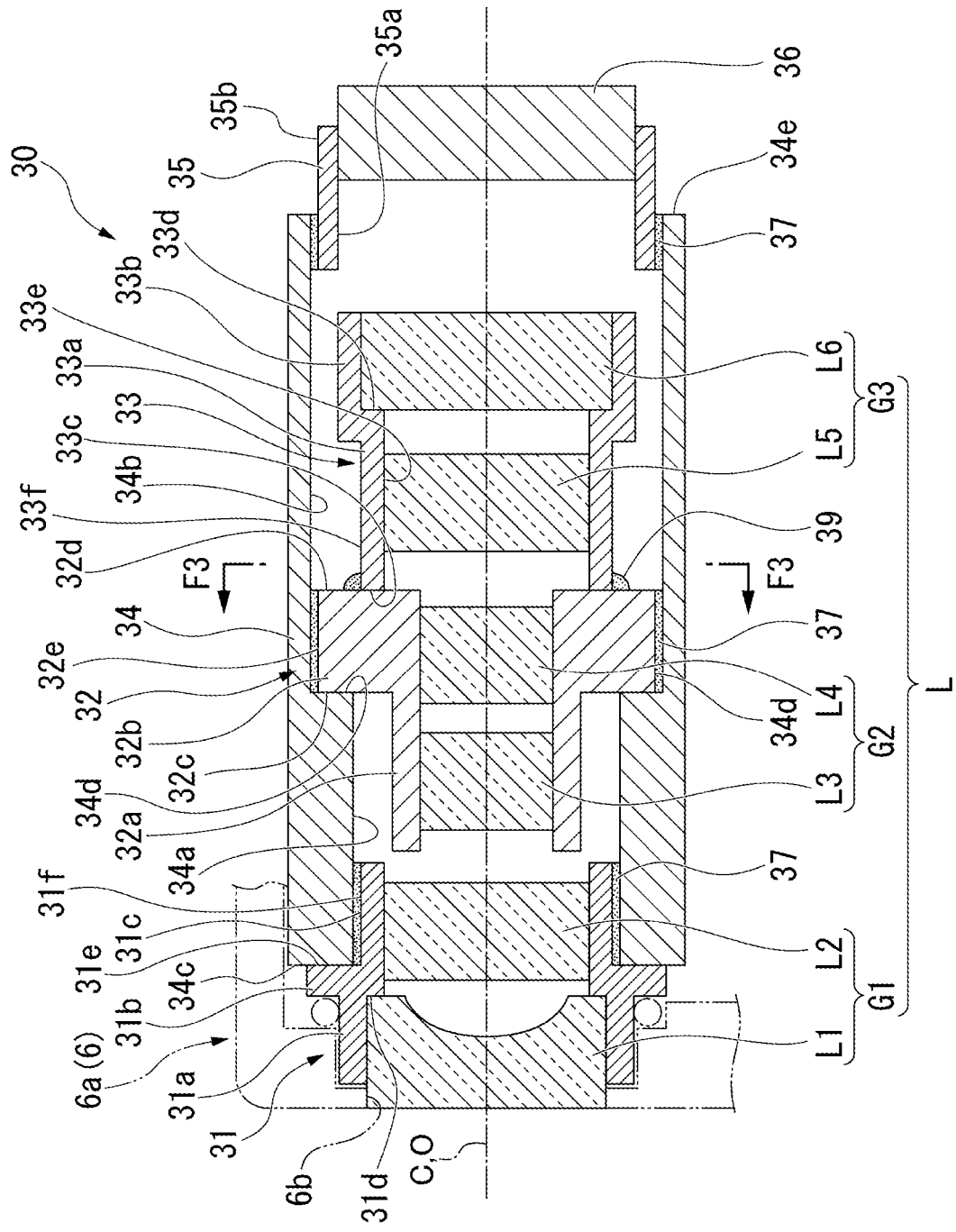
FIG. 2 is a schematic cross-sectional view showing an example of an imaging unit according to the first embodiment of the present invention.
Figure 3:
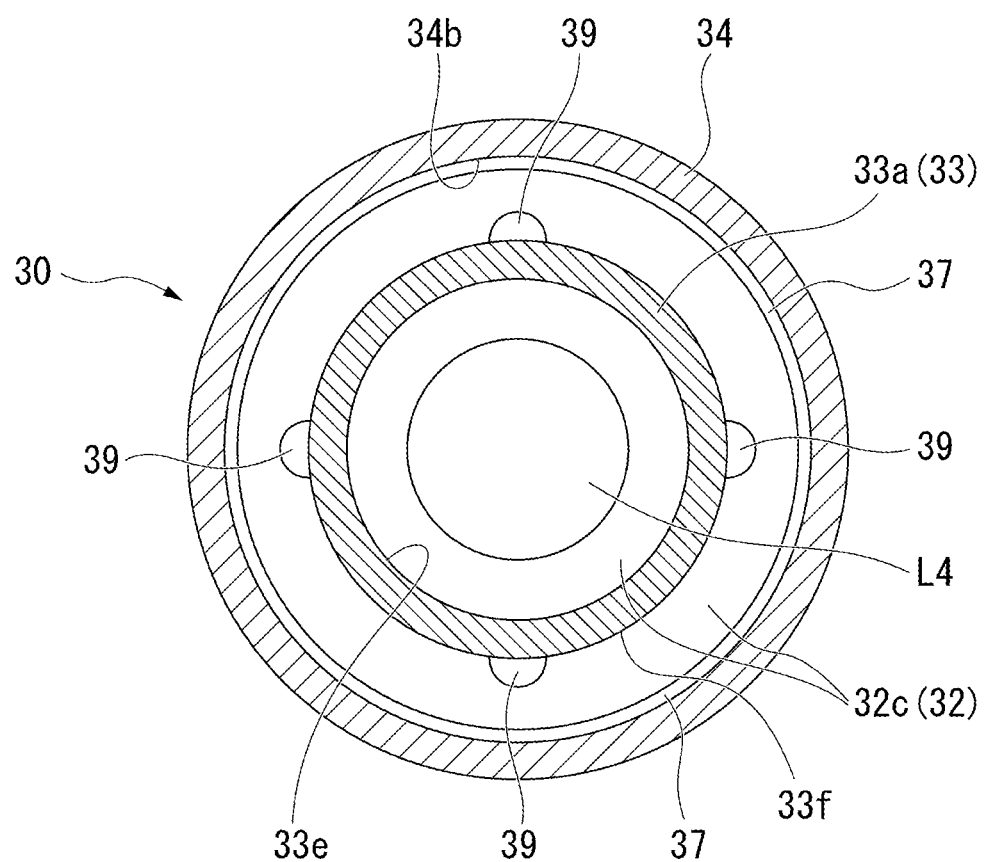
FIG. 3 is a cross-sectional view taken along line F3-F3 in FIG. 2.

FIG. 2 is a schematic cross-sectional view showing an example of an imaging unit according to the first embodiment of the invention. FIG. 3 is a cross-sectional view taken along line F3-F3 in FIG. 2.

As shown in FIG. 2, a hard distal end cover 6a that forms the distal end face and side face of the distal end portion 6 is arranged at the distal end (left side in the figure) of the distal end portion 6.

The imaging unit 30 is arranged inside the distal end portion 6 so as to face the observation window 6b formed in the distal end cover 6a forming the distal end surface and the side surface of the distal end portion 6.

The shape of the imaging unit 30 is generally columnar extending from the distal end of the distal end portion 6 toward the proximal end.

The imaging unit 30 has an objective lens L, a first front lens group frame 31, a second front lens group frame 32 (first lens frame), a rear group lens frame 33 (second lens frame), a first holding frame 34 (holder), a second holding frame 35 (holder), and an imaging element 36.

The objective lens L is an imaging optical system that forms an image of the subject. The lens configuration of the objective lens L is not particularly limited as long as it has a positive refractive power as a whole and can form an image of the subject on the imaging surface of the imaging element 36.

In the example shown in FIG. 2, the objective lens L consists of a first front lens group G1, a second front lens group G2 (first lens), and a rear lens group G3 (second lens). The first front lens group G1, the second front lens group G2, and the rear lens group G3 are arranged in this order from the object side to the image side.

The optical axis O of the objective lens L is parallel to the central axis C of the outer shape of the imaging unit 30. In the example shown in FIG. 2, the optical axis O and the central axis C are coaxial.

The direction from the object side to the image side of the objective lens L coincides with the direction from the distal end to the proximal end of the distal end portion 6.

The first front lens group G1 closest to the object side in the objective lens L is arranged near the distal end of the distal end portion 6 facing the observation window 6b.

The objective lens L may be a fixed focus lens, a lens capable of adjusting focus, or a lens having a magnification adjustment function or a zoom variable power function.

In the example shown in FIG. 2, the objective lens L is a fixed focus lens.

For example, the first front lens group G1 is composed of a first lens L1 and a second lens L2. The first lens L1 and the second lens L2 are arranged in this order from the object side to the image side. However, the first front lens group G1 may be composed of a single lens, a cemented lens, three or more lenses, or the like, if necessary.

For example, the second front lens group G2 is composed of a third lens L3 and a fourth lens L4. The third lens L3 and the fourth lens L4 are arranged in this order from the object side to the image side. However, the second front lens group G2 may be composed of a single lens, a cemented lens, three or more lenses, or the like, if necessary.

The rear group lens G3 is composed of a fifth lens L5 and a sixth lens L6. The first lens L1 and the second lens L2 are arranged in this order from the object side to the image side. However, the rear lens group G3 may be composed of a single lens, a cemented lens, three or more lenses, or the like, if necessary.

In the following, for the sake of simplification, when collectively referring to lenses with serial numbers among the first lens L1, the second lens L2, the third lens L3, the fourth lens L4, the fifth lens L5, and the sixth lens L6, the suffix of L may be referred to as "lens Ln-Lm" (where n and m are integers where n<m).

For example, "lenses L1-L6" represent the first lens L1, the second lens L2, the third lens L3, the fourth lens L4, the fifth lens L5, and the sixth lens L6.

For example, "lens L1-L2" represents the first lens L1 and the second lens L2, and corresponds to the first front group lens G1 in this embodiment.

In the objective lens L, the configuration of the lenses L1-L6 is not particularly limited as long as the optical characteristics required for the objective lens L can be obtained.

In FIG. 2, for the sake of simplicity, the concave and convex shapes of the optical surfaces of the lenses L1 to L6 are exaggerated or omitted.

For example, the first lens L1 is drawn in the shape of a plano-concave lens, because in the case of an objective lens used in an endoscope, a lens having negative refractive power is often used as the first lens L1. However, the lens having negative refractive power is not limited to a plano-convex lens.

A lens having positive refractive power may be used as the first lens L1.

In FIG. 2, the optical surfaces of the lenses L2-L6 are all drawn as flat surfaces. However, each optical surface of the lenses L2-L6 is formed in any one of convex, concave, and planar shapes so that the objective lens L can obtain the required refractive power.

A single lens or a cemented lens may be used for each of the lenses L1 to L6.

The relative diameter of each of the lenses L1-L6 in FIG. 2 is an example. The diameters of each of the lenses L1-L6 is not limited to the diameter ratio shown in FIG. 2.

In the following, an example in which the diameter of each of the lenses L3-L4 is the smallest and the lens diameters of lenses L1-L2 and lenses L5-L6 are larger than that of lenses L3-L4 will be described.

The first front lens group frame 31 holds the first front lens group G1 composed of the first lens L1 and the second lens L2.

The shape of the first front group lens frame 31 is a cylindrical body as a whole, and is not particularly limited as long as the first lens L1 and the second lens L2 can be coaxially held inside. FIG. 2 shows an example of the first front lens group frame 31 when the lens outer diameter of the first lens L1 is larger than the lens outer diameter of the second lens L2.

The first front group lens frame 31 has a first cylindrical portion 31a, a second cylindrical portion 31c, and a flange portion 31b.

The first cylindrical portion 31a is a cylindrical portion that holds the outer peripheral portion of the first lens L1.

The second cylindrical portion 31c is a cylindrical portion that holds the second lens L2 at a position closer to the image side than the first lens L1. The second cylindrical portion 31c extends further toward the image side from the image-side end (the right end in the drawing) of the first cylindrical portion 31a.

The central axis of the first cylindrical portion 31a and the central axis of the second cylindrical portion 31c are coaxial.

A stepped portion 31d extending radially inward from the inner peripheral surface of the first cylindrical portion 31a is formed at the connecting portion between the first cylindrical portion 31a and the second cylindrical portion 31c.

The stepped portion 31d is a flat surface perpendicular to the central axis of the first cylindrical portion 31a and facing the object side. The stepped portion 31d positions the first lens L1 in the axial direction of the first front group lens frame 31 by coming into contact with the image-side end face of the first lens L1.

A side surface 31f, which is an outer peripheral surface of the second cylindrical portion 31c, is used for radial positioning with respect to the first holding frame 34 and fixing to the first holding frame 34, which will be described later.

The flange portion 31b is a flat plate extending outward from the outer peripheral portions of the first tubular portion 31a and the second tubular portion 31c at the connecting portion between the first tubular portion 31a and the second tubular portion 31c. The outer shape of the flange portion 31b seen from the axial direction of the first front group lens frame 31 is, for example, an annular shape.

An image-side end face 31e of the flange portion 31b is a plane perpendicular to the central axis of the first cylindrical portion 31a. The end face 31 e is used for positioning the first front group lens frame 31 in the axial direction of the imaging unit 30.

The position of the end face 31e with respect to the stepped portion 31d in the axial direction of the first front lens group frame 31 is determined in advance according to the design value of the distance in the axial direction between the first front lens group G1 and the second front lens group G2 when the imaging unit 30 is assembled.

In the first front group lens frame 31, the first lens L1 is inserted inside the first cylindrical portion 31a. In the example shown in FIG. 2, the object-side end of the first lens L1 protrudes further toward the object than the first cylindrical portion 31a. The first lens L1 protruding from the first cylindrical portion 31a is inserted inside the observation window 6b.

The first lens L1 is fixed to the first front group lens frame 31 in a state where the position in the radial direction is restricted by the first cylindrical portion 31a and the position in the optical axis direction is restricted by the stepped portion 31d. A fixing method of the first lens L1 is not particularly limited. For example, the first lens L1 may be fixed to the first front group lens frame 31 with an adhesive.

In the first front group lens frame 31, the second lens L2 is inserted inside the second cylindrical portion 31c. The second lens L2 is fixed to the first front lens group frame 31 with its position in the radial direction restricted by the second cylindrical portion 31c. A fixing method of the second lens L2 is not particularly limited. For example, the second lens L2 may be fixed to the first front group lens frame 31 with an adhesive.

The second lens L2 may be fixed in a state of being positioned by abutting against a positioning portion in the optical axis direction similar to the stepped portion 31d of the first front group lens frame 31, or may be fixed to the second cylindrical portion 31c after being adjusted in the optical axis direction within the second cylindrical portion 31c.

The second front lens group frame 32 holds the second front lens group G2 consisting of the third lens L3 and the fourth lens L4.

The shape of the second front group lens frame 32 is a cylindrical body as a whole, and is not particularly limited as long as the third lens L3 and the fourth lens L4 can be coaxially held inside. FIG. 2 depicts an example in which the lens outer diameters of the third lens L3 and the fourth lens L4 are equal to each other.

The second front group lens frame 32 has a lens barrel 32a and a flange portion 32b.

The lens barrel 32a is a cylindrical portion that holds the outer peripheral portions of the third lens L3 and the fourth lens L4.

However, if the outer diameters of the third lens L3 and the fourth lens L4 are different from each other, the inner peripheral surface of the lens barrel 32a may be divided into a plurality of cylindrical surfaces according to the outer diameters of the third lens L3 and the fourth lens L4. In this case, similarly to the first front group lens frame 31, the inner peripheral surface of the lens barrel 32a may be provided with a stepped portion or a protrusion for positioning at least one of the third lens L3 and the fourth lens L4 in the optical axis direction.

The flange portion 32b is a flat plate extending outward from the outer peripheral portion of the lens barrel 32a. The outer shape of the flange portion 32b seen from the axial direction of the second front group lens frame 32 is, for example, an annular shape.

The first end face 32c on the object side and the second end face 32d on the image side of the flange portion 32b are both planes perpendicular to the central axis of the lens barrel 32a.

A side surface 32e, which is an outer peripheral surface of the flange portion 32b sandwiched between the first end surface 32c and the second end surface 32d, is a cylindrical surface coaxial with the lens barrel 32a.

The first end face 32c is used for positioning the second front group lens frame 32 in the axial direction of the imaging unit 30.

The second end face 32d is used for positioning the rear lens group frame 33 in the axial direction of the imaging unit 30 and for fixing it to the rear lens group frame 33. The position of the second end face 32d relative to the first end face 32c in the axial direction is determined in advance according to the design value of the air gap between the fourth lens L4 and the fifth lens L5 when the imaging unit 30 is assembled.

The side surface 32e is used for radial positioning with respect to the first holding frame 34 and fixing to the first holding frame 34, which will be described later.

In the second front group lens frame 32, a third lens L3 and a fourth lens L4 are inserted inside the lens barrel 32a. The third lens L3 and the fourth lens L4 are fixed to the second front group lens frame 32 while being positioned at a predetermined position in the optical axis direction with respect to the first end face 32c.

The fixing method of the third lens L3 and the fourth lens L4 is not particularly limited. For example, the third lens L3 and the fourth lens L4 may be fixed to the second front group lens frame 32 with an adhesive.

As a method for positioning the third lens L3 and the fourth lens L4 in the optical axis direction, abutting against the positioning portion or position adjustment can be adopted as in the case of the first front group lens frame 31.

The rear lens group frame 33 holds the rear lens group G3 consisting of the fifth lens L5 and the sixth lens L6.

The shape of the rear group lens frame 33 is a cylindrical body as a whole, and is not particularly limited as long as it can coaxially hold the fifth lens L5 and the sixth lens L6 inside. FIG. 2 illustrates an example of the rear lens group frame 33 in which the lens outer diameter of the fifth lens L5 is smaller than the lens outer diameter of the sixth lens L6.

The rear group lens frame 33 has a first cylindrical portion 33a and a second cylindrical portion 33b.

The first cylindrical portion 33a is a cylindrical portion that holds the outer peripheral portion of the fifth lens L5.

The inner diameter of the first cylindrical portion 33a is larger than the inner diameter of the lens barrel 32a of the second front group lens frame 32 and smaller than the outer shape of the flange portion 32b.

The second cylindrical portion 33b is a cylindrical portion that holds the sixth lens L6 at a position closer to the image side than the fifth lens L5. The second cylindrical portion 33b extends further toward the image side from the image-side end of the first cylindrical portion 33a.

The outer diameter of the second cylindrical portion 33b is smaller than the outer diameter of the flange portion 32b of the second front group lens frame 32.

The central axis of the first cylindrical portion 33a and the central axis of the second cylindrical portion 33b are coaxial.

A stepped portion 33d extending radially outward from the inner peripheral surface of the first cylindrical portion 33a is formed at the connecting portion between the first cylindrical portion 33a and the second cylindrical portion 33b.

The stepped portion 33d is a plane perpendicular to the central axis of the first cylindrical portion 33a and facing the image side. The stepped portion 33d positions the sixth lens L6 in the axial direction of the rear lens group frame 33 by coming into contact with the object-side end surface of the sixth lens L6.

The object-side end face 33c of the first cylindrical portion 33a is a plane perpendicular to the central axis of the rear lens group frame 33.

In the rear group lens frame 33, the fifth lens L5 is inserted into the inner peripheral surface 33e of the first cylindrical portion 33a. The fifth lens L5 is fixed to the second front lens group frame 32 while being positioned at a predetermined position in the optical axis direction with respect to the end surface 33c and the stepped portion 33d.

The fixing method of the fifth lens L5 is not particularly limited. For example, the fifth lens L5 may be fixed to the rear lens group frame 33 with an adhesive.

As a method for positioning the fifth lens L5 in the optical axis direction, it is possible to employ abutment against a positioning portion or position adjustment in the same manner as the first front group lens frame 31.

In the rear group lens frame 33, the sixth lens L6 is inserted inside the second cylindrical portion 33b.

The sixth lens L6 is fixed to the rear lens group frame 33 with its position in the radial direction restricted by the second cylindrical portion 33b and its position in the optical axis direction restricted by the stepped portion 33d. A fixing method of the sixth lens L6 is not particularly limited. For example, the sixth lens L6 may be fixed to the rear lens group frame 33 with an adhesive.

The rear lens group frame 33 is fixed to the second front lens group frame 32 with a hardened adhesive 39 in a state where the position of the end face 33c is restricted in the axial direction by the second end face 32d of the second front lens group frame 32. Therefore, the rear lens group frame 33 is fixed to the second front lens group frame 32 with the end face 33c in contact with the second end face 32d, or with a cured thin layer of adhesive 39 interposed between the end face 33c and the second end face 32d.

The adhesive 39 is not particularly limited as long as the necessary adhesive strength is obtained after curing. For example, as the adhesive 39, an ultraviolet curable adhesive, a thermosetting adhesive, welding, soldering, brazing, or the like may be used.

The arrangement positions of the second front lens group frame 32 and the adhesive 39 with respect to the second front lens group frame 32 are not particularly limited.

In the example shown in FIG. 2, the adhesive 39 is cured after being applied to the corner formed by the outer peripheral surface 33f of the first tubular portion 33a and the second end surface 32d. The adhesive 39 may be applied over the entire circumference of the outer peripheral surface 33f, or may be applied at a plurality of locations spaced apart in the circumferential direction. However, if the fixing position is likely to change due to shrinkage of the adhesive 39 during hardening, it is more preferable to apply the adhesive 39 to a plurality of locations spaced apart in the circumferential direction.

For example, in the example shown in FIG. 3, the cured adhesive 39 is formed at four locations dividing the first cylindrical portion 33a in the circumferential direction into approximately four portions.

The fixed position of the rear lens group frame 33 in the radial direction is the position where the optical axis of the rear lens group G3 is coaxial with the optical axis O when the respective optical axes of the first front lens group G1 and the second front lens group G2 are arranged to be coaxial with the designed optical axis O. However, in the present embodiment, the rear lens group frame 33 is fixed in a position adjusted so that the imaging performance of the objective lens L is good according to manufacturing and assembly errors of the first front lens group G1 and the second front lens group G2.

As shown in FIG. 2, the first holding frame 34 houses the second front lens group frame 32 and the rear lens group frame 33 inside. Inside the first holding frame 34, the second front group lens frame 32 is fixed to the first holding frame 34 at the flange portion 32b. Inside the first holding frame 34, the rear lens group frame 33 is radially separated from the first holding frame 34. Therefore, the rear lens group frame 33 is accommodated inside the first holding frame 34 without contacting the first holding frame 34 and with a gap with respect to the first holding frame 34.

The shape of the first holding frame 34 is not particularly limited as long as it can fix the second front lens group frame 32 as described above and accommodate the second front lens group frame 32 and the rear lens group frame 33 inside.

In the example shown in FIG. 2, the first holding frame 34 is a cylindrical frame longer than the total length of the assembly of the second front group lens frame 32 and rear group lens frame 33 fixed to each other. However, the inner peripheral surface of the first holding frame 34 has a first inner peripheral surface 34a and a second inner peripheral surface 34b in this order along the axial direction from the front-end surface 34c of the first holding frame 34 to the rear end surface 34e.

The first inner peripheral surface 34a is a cylindrical surface having a diameter larger than the outer diameter of the lens barrel 32a and smaller than the outer diameter of the flange portion 32b. In the example shown in FIG. 2, the first inner peripheral surface 34a fixes the first front lens group frame 31 while restricting the position of the first front lens group frame 31 in the radial direction. In this case, the diameter of the first inner peripheral surface 34 a is slightly larger than the outer diameter of the second cylindrical portion 31c of the first front lens group frame 31.

The distal end surface 34c is a plane perpendicular to the central axis of the first inner peripheral surface 34a.

The second inner peripheral surface 34b is a cylindrical surface coaxial with the first inner peripheral surface 34a. The second inner peripheral surface 34b fixes the flange portion 32b while regulating the radial positions of the first inner peripheral surface 34a and the concentric flange portion 32b.

The diameter of the second inner peripheral surface 34b is slightly larger than the diameter of the side surface 32e. Therefore, a stepped portion 34d is formed between the first inner peripheral surface 34a and the second inner peripheral surface 34b.

The stepped portion 34d is a plane perpendicular to the central axis of the first inner peripheral surface 34a. The stepped portion 34 d is used for axial positioning of the second front group lens frame 32 with respect to the first holding frame 34.

The second front group lens frame 32 is fixed to the second inner peripheral surface 34b of the first holding frame 34 with the first end surface 32c in contact with the stepped portion 34d of the first holding frame 34. A fixing method of the second front group lens frame 32 is not particularly limited. In the example shown in FIG. 2, it is fixed by an adhesive 37 interposed between the side surface 32e and the second inner peripheral surface 34b. The type of adhesive 37 is not particularly limited. For example, as adhesive 37, an adhesive similar to the adhesive suitable for adhesive 39 may be used.

The first front group lens frame 31 is fixed to the first inner peripheral surface 34a at the distal end of the first holding frame 34.

The first front group lens frame 31 is fixed to the first inner peripheral surface 34a of the first holding frame 34 with the end surface 31e in contact with the distal end surface 34c of the first holding frame 34. A fixing method of the first front group lens frame 31 is not particularly limited. In the example shown in FIG. 2, the first front group lens frame 31 is fixed to the first holding frame 34 with an adhesive 37 interposed between the side surface 31f and the first inner peripheral surface 34a.

However, the first end surface 32c and the stepped portion 34d do not need to be in contact with each other as long as the positions are adjusted so that the distance in the axial direction between the first front lens group G1 and the second front lens group G2 is a predetermined value.

The second holding frame 35 holds an imaging element 36, which will be described later. The shape of the second holding frame 35 is not particularly limited as long as it can hold the imaging element 36 and can be fixed to the rear end portion of the first holding frame 34.

In the example shown in FIG. 2, the second holding frame 35 has a cylindrical shape with an inner peripheral surface 35a having an inner diameter capable of holding the imaging element 36 inside, and an outer peripheral surface 35b having an outer diameter slightly smaller than the diameter of the second inner peripheral surface 34b.

The second holding frame 35 is inserted into the rear end portion of the second inner peripheral surface 34b of the first holding frame 34, and is fixed to the second inner peripheral surface 34b in a state in which the position in the radial direction is positioned.

A fixing method of the second holding frame 35 is not particularly limited. In the example shown in FIG. 2, the second holding frame 35 is fixed to the first holding frame 34 with an adhesive 37 interposed between the outer peripheral surface 35b and the second inner peripheral surface 34b.

The imaging element 36 captures an image of the subject formed by the objective lens L. For example, a CCD, CMOS sensor, or the like may be used as the imaging element 36.

The imaging element 36 is fixed inside the second holding frame 35 with the imaging element chip held by an appropriate holding member. The imaging element 36 may include a cover glass if desired.

The imaging element 36 is electrically connected to an electric cable inside the insertion portion 9. An image signal generated by the imaging element 36 is sent to the video processor 4 through an electric cable and displayed on the color monitor 5.

Such an imaging unit 30 can be manufactured, for example, as follows.

Figure 4:
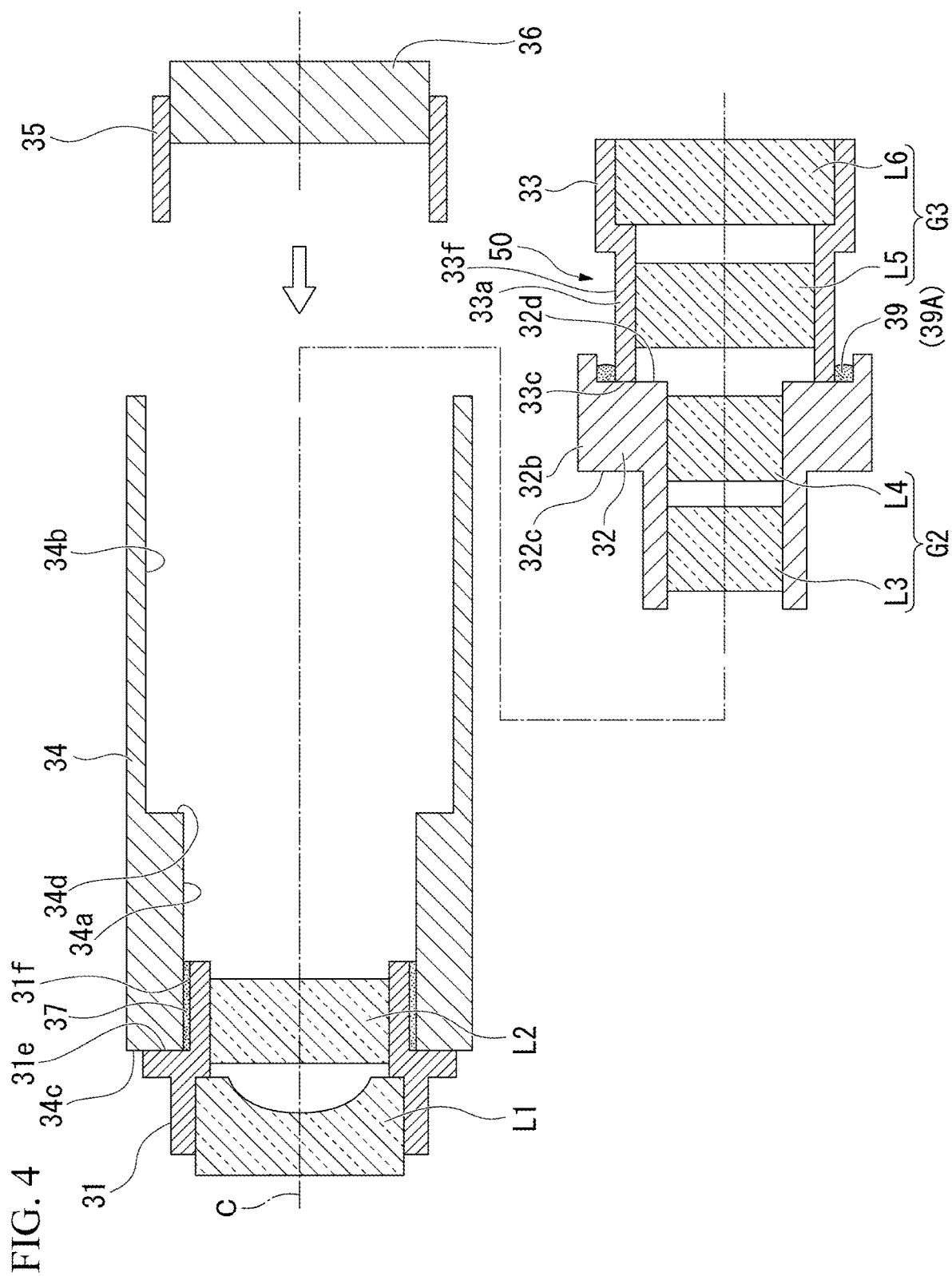
FIG. 4 is a schematic cross-sectional view showing an example of a method for manufacturing the imaging unit according to the first embodiment of the present invention.

FIG. 4 is a schematic cross-sectional view showing an example of the manufacturing method of the imaging unit according to the first embodiment of the present invention.

First, the lenses L1-L2 are fixed to the first front group lens frame 31, the lenses L3-L4 are fixed to the second front group lens frame 32, and the lenses L5-L6 are fixed to the rear group lens frame 33. The imaging element 36 is fixed to the second holding frame 35 as shown in FIG. 2.

At this time, when the lenses L1-L2 are fixed to the first front lens group frame 31, they are fixed so that their relative positions in the axial direction and the radial direction are the same as the relative positions of the objective lens L. When the lenses L3 and L4 are fixed to the second front lens group frame 32, they are fixed so that their axial and radial relative positions are the same as those of the objective lens L. When the lenses L5 and L6 are fixed to the rear lens group frame 33, they are fixed so that their axial and radial relative positions are the same as those of the objective lens L.

After that, as shown in FIG. 4, the first front group lens frame 31 is fixed to the first holding frame 34 using an adhesive 37.

The first front group lens frame 31 is fixed in a state in which the first cylindrical portion 31a is inserted into the first inner peripheral surface 34a and the end surface 31e is in contact with the distal end surface 34c, thereby positioning the positions in the axial direction and the radial direction with respect to the first holding frame 34.

The second front lens group frame 32 and the rear lens group frame 33 are adjusted and fixed to each other so that the optical axis of the second front lens group G2 and the optical axis of the rear lens group G3 are coaxial. Thus, an assembly 50 is formed.

For example, the assembly 50 may be formed as follows.

The end surface 33c of the rear lens group frame 33 abuts against the second end surface 32d of the second front lens group frame 32 held by an adjustment jig (not shown). The rear lens group frame 33 is held so as to be relatively movable with respect to the second front lens group frame 32.

A measurement light beam for protruding an adjustment image is made incident along the designed optical axis of the second front lens group G2, and an adjustment imaging element is arranged on the image plane of the optical system composed of the second front lens group G2 and the rear lens group G3.

The measurer moves the rear lens group frame 33 in the radial direction while observing the image of the measurement light flux acquired by the adjustment imaging element, and adjusts the position of the rear lens group frame 33 so as to obtain good imaging performance. This reduces the aberration of the optical system constituted by the second front lens group G2 and the rear lens group G3.

At this time, if the end surface 33c of the rear lens group frame 33 moves while being in contact with the second end surface 32d of the second front lens group frame 32, the second end surface 32d functions as a positioning surface for the rear lens group frame 33 in the axial direction.

However, the rear group lens frame 33 may be moved apart from the second end face 32d as long as the distance can be fixed by the interposition of the adhesive 39. In this case, it is also possible to adjust the position of the rear lens group frame 33 in the axial direction.

After the position adjustment is completed, an uncured adhesive 39A is applied to an appropriate position of the corner formed by the outer peripheral surface 33f of the first cylindrical portion 33a and the second end surface 32d. However, when the end face 33c is separated from the second end face 32d, the adhesive 39A is applied so as to fill between the end face 33c and the second end face 32d.

After that, the adhesive 39A is cured. For example, when the adhesive 39A is an ultraviolet curable adhesive, the adhesive 39A is cured by irradiating ultraviolet rays.

For example, if the adhesive 39A is a thermosetting adhesive, the heater heats the adhesive 39A to cure the adhesive 39A.

When the adhesive 39A is cured to form the cured adhesive 39, the fixing of the rear group lens frame 33 is completed, and the assembly 50 is formed.

After that, the assembly 50 is inserted into the first holding frame 34 from the second inner peripheral surface 34b. The flange portion 32b is inserted into the second inner peripheral surface 34b, and the first end surface 32c is brought into contact with the stepped portion 34d. Thereby, the position of the assembly 50 in the axial direction and the radial direction with respect to the first holding frame 34 is determined.

In the present embodiment, the distance in the axial direction between the distal end surface 34c and the end surface 34d is predetermined so that the positions of the second lens L2 and the third lens L3 in the optical axis direction are the design values.

In this manner, the lenses L1-L6 are arranged inside the first holding frame. Thereafter, an uncured adhesive 37 (not shown) is applied to the gap between the flange portion 32b and the second inner peripheral surface 34b and cured. At this time, the radial position of the assembly 50 may be determined without adjustment by the fitting between the flange portion 32b and the second inner peripheral surface 34b. However, the adhesive 37 may be hardened after the radial position is adjusted in the range of the gap by securing a sufficient gap between the flange portion 32b and the second inner peripheral surface 34b. In this case, it is possible to adjust the position of the assembly 50 in the radial direction within the range of the clearance.

The adjustment in the radial direction can be performed in the same manner as the adjustment in the radial direction of the second front lens group G2 and the rear lens group G3.

After that, the second holding frame 35 to which the imaging element 36 is fixed is inserted into the second inner peripheral surface 34b, and the second holding frame 35 is fixed to the first holding frame 34 with the adhesive 37 while the imaging surface of the imaging element 36 is aligned with the image plane of the objective lens L.

The position of the second holding frame 35 may be determined by pressing against a positioning portion provided on the first holding frame 34, or may be determined by adjusting the position. The position adjustment may be performed, for example, by holding the second holding frame 35 with an appropriate adjustment jig and observing an image captured by the imaging element 36.

When the second holding frame 35 is fixed, the imaging unit 30 as shown in FIG. 2 is manufactured.

According to the manufacturing method of this embodiment, the imaging unit 30 is formed by inserting the assembly 50 in which the relative positions of the second front lens group G2 and the rear lens group G3 are adjusted, into the first holding frame. As a result, an increase in the aberration of the objective lens L due to manufacturing errors and assembly errors in each component is suppressed.

The imaging unit 30 of this embodiment described above is an imaging unit of an endoscope that is arranged and used at the distal end portion 6 of the endoscope 2.

The second front lens group G2 and the rear lens group G3 are examples of a first lens and a second lens included in the objective lens L, respectively.

The second front group lens frame 32 is an example of a first lens frame that holds the first lens.

The rear group lens frame 33 is an example of a second lens frame that is fixed to the first lens frame and holds the second lens.

The first holding frame 34 and the second holding frame 35 fixed to the first holding frame 34 are an example of a holder that accommodates the first lens frame and the second lens frame inside and holds the first lens frame.

In the imaging unit 30, the second lens frame is fixed to the first lens frame without contacting the imaging element 36 and the holder and with a gap between the imaging element 36 and the holder.

In the imaging unit 30, the first front group lens G1, the second front group lens G2, and the rear group lens G3 inside the first front group lens frame 31, the second front group lens frame 32, and the rear group lens frame 33 are firmly fixed to the first front group lens frame 31, the second front group lens frame 32, and the rear group lens frame 33, respectively, on the side surfaces of the respective lenses.

However, the second front lens group frame 32 and the rear lens group frame 33 are fixed with an adhesive 39 with the second end face 32d and the end face 33c facing each other in the axial direction. Therefore, for example, if an external force acts on the rear end portion of the rear lens group frame 33, the hardened adhesive 39 may be deformed and the rear lens group frame 33 may be displaced, or the adhesive strength may be reduced and the rear lens group frame 33 may come off the second end surface 32d.

In the imaging unit 30, the rear lens group frame 33 is fixed to the second front lens group frame 32, and is arranged inside the holder while being separated from the holder. The rear lens group frame 33 is not in contact with the holder, and the rear lens group frame 33 is arranged with a gap with respect to the holder. As a result, even if a load that deforms the holder due to, for example, an external force or heat is applied to the holder, the load received by the holder is not directly transmitted to the rear lens group frame 33 spaced apart inside the first holding frame 34. As a result, since the fixed portion formed by the adhesive 39 is prevented from being displaced or damaged, the optical performance such as the imaging performance of the objective lens L adjusted when the rear group lens frame 33 is fixed is maintained.

In this embodiment, the rear lens group frame 33 is also spaced apart from the image sensor 36 fixed to the holder, is not in contact with the image sensor 36, and is spaced apart from the image sensor 36. Therefore, even if an external force acts on the imaging element 36 or the second holding frame 35 is deformed by heat, the fixed portion formed by the adhesive 39 is prevented from being deformed or damaged.

In the imaging unit 30, a portion of the first front group lens frame 31 closer to the object side than the flange portion 31b protrudes outside the first holding frame. However, in the first front group lens frame 31, the second cylindrical portion 31c is inserted into the first inner peripheral surface 34a, and is fixed by interposing an adhesive 37 between the outer peripheral surface of the second cylindrical portion 31c and the first inner peripheral surface 34a. As a result, the first front group lens frame 31 is firmly fixed to the first holding frame 34. Therefore, even if the first front lens group frame 31 receives a load such as an external force, the relative positional relationship between the first front lens group G1 and the second front lens group G2 and rear lens group G3 is prevented from changing.

As described above, according to the imaging unit 30 and the endoscope 2 of the present embodiment, it is easy to maintain the optical performance even if a load is applied to the holder arranged radially outside the objective lens.

[First Modification]

An imaging unit of an endoscope according to a modified example (first modified example) of the first embodiment of the present invention will be described.

Figure 5:
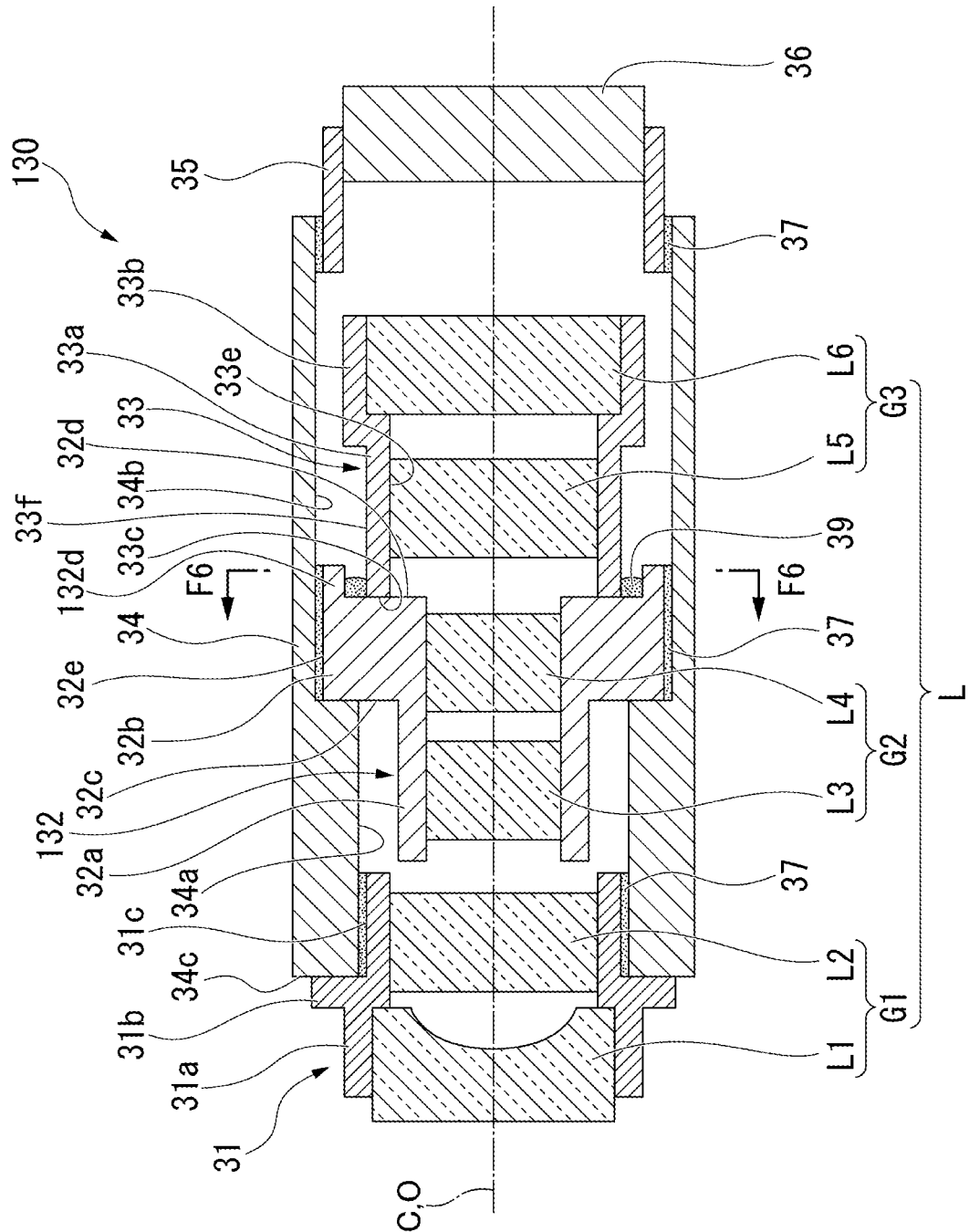
FIG. 5 is a schematic cross-sectional view showing an example of an imaging unit according to a modified example (first modified example) of the first embodiment of the present invention.
Figure 6:
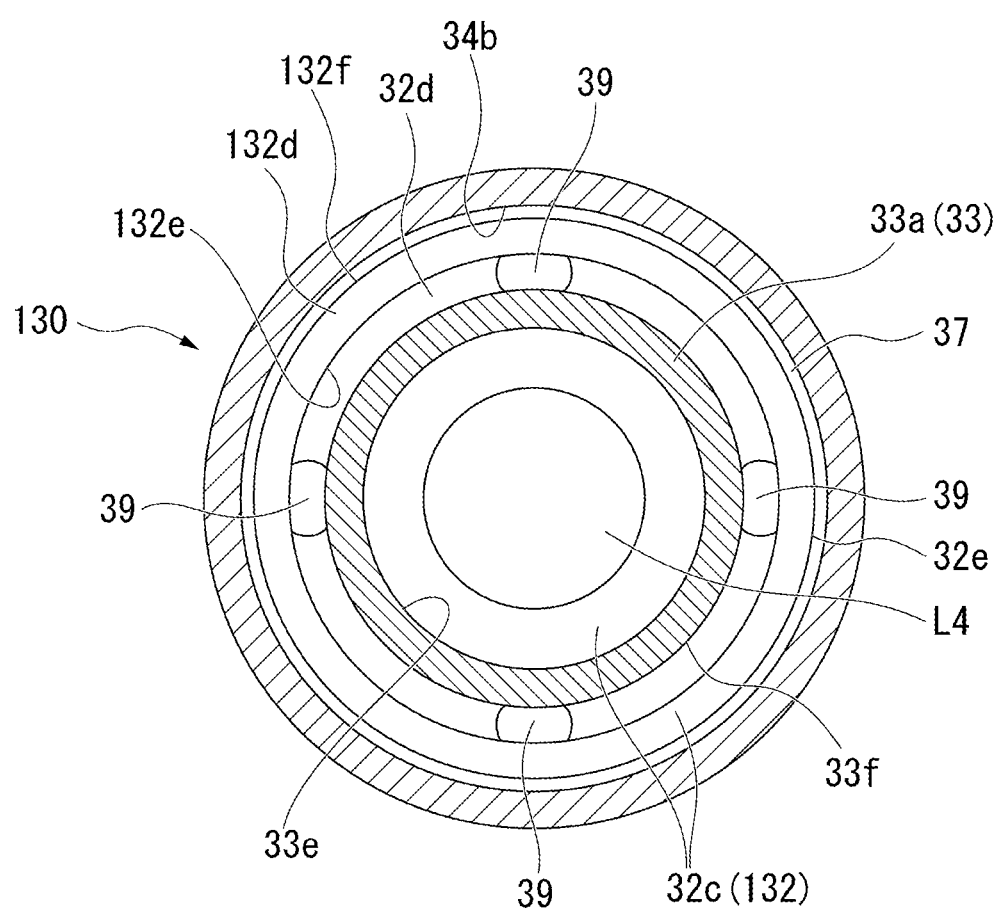
FIG. 6 is a cross-sectional view taken along line F6-F6 in FIG. 5.

FIG. 5 is a schematic cross-sectional view showing an example of an imaging unit according to a modified example (first modified example) of the first embodiment of the present invention. FIG. 6 is a cross-sectional view taken along line F6-F6 in FIG. 5.

As shown in FIG. 5, an imaging unit 130 (imaging unit of an endoscope) according to this modified example has a second front group lens frame 132 (first lens frame) instead of the second front group lens frame 32 of the imaging unit 30 according to the first embodiment.

As shown in FIG. 1, the imaging unit 130 can be used in place of the imaging unit 30 in the endoscope 2 according to the first embodiment.

The following description will focus on points that differ from the first embodiment.

As shown in FIG. 5, the second front lens group frame 132 is the same as the second front lens group frame 32 except that it further has a protrusion 132d protruding from the second end face 32d of the flange portion 32b of the second front lens group frame 32.

The protrusion 132d protrudes in the axial direction at a position where the first cylindrical portion 33a of the rear lens group frame 33 can be arranged radially inward. The arrangement position of the protrusion 132d in the circumferential direction is not particularly limited as long as it is arranged at a position overlapping the portion to which the adhesive 39 is applied when viewed from the radial direction.

In the example shown in FIG. 6, the protrusion 132d is an annular protrusion formed on the outer peripheral portion of the flange portion 32b when viewed from the axial direction. The diameter of the inner peripheral surface 132e of the protrusion 132d is larger than the outer diameter of the first cylindrical portion 33a. In the example shown in FIG. 6, the outer peripheral surface 132f of the protrusion 132d is formed by extending the side surface 32e in the axial direction. However, the outer diameter of the protrusion 132d may be smaller than the diameter of the side surface 32e.

In this modified example, the adhesive 39 is applied along the groove surrounded by the outer peripheral surface 33f, the second end surface 32d, and the inner peripheral surface 132e of the protrusion 132d. For this reason, the adhesive 39 hardens in a state in which it is in close contact with the outer peripheral surface 33f and the inner peripheral surface 132e as well as the corner formed by the outer peripheral surface 33f and the first end surface 32c.

That is, in this modified example, the rear lens group frame 33 is fixed to the protrusion 132d with the adhesive 39 at the portion overlapping the protrusion 132d when viewed in the radial direction.

The imaging unit 130 can be manufactured in the same manner as the imaging unit 30 of the first embodiment except that the second front group lens frame 132 is used instead of the second front group lens frame 32 and the adhesive 39 is applied between the first cylindrical portion 33a and the protrusion 132d.

According to the imaging unit 130 of this modified example, the adhesive 39 applied between the first cylindrical portion 33a and the protrusion 132d is cured, so that the rear lens group frame 33 is adhered to the protrusion 132d in the radial direction. As a result, the rear lens group frame 33 is fixed more firmly in the radial direction, so that even if a load is applied to the holder arranged radially outside the objective lens, it becomes easier to maintain the optical performance.

[Second Modification]

An imaging unit of an endoscope according to a modified example (second modified example) of the first embodiment of the present invention will be described.

Figure 7:
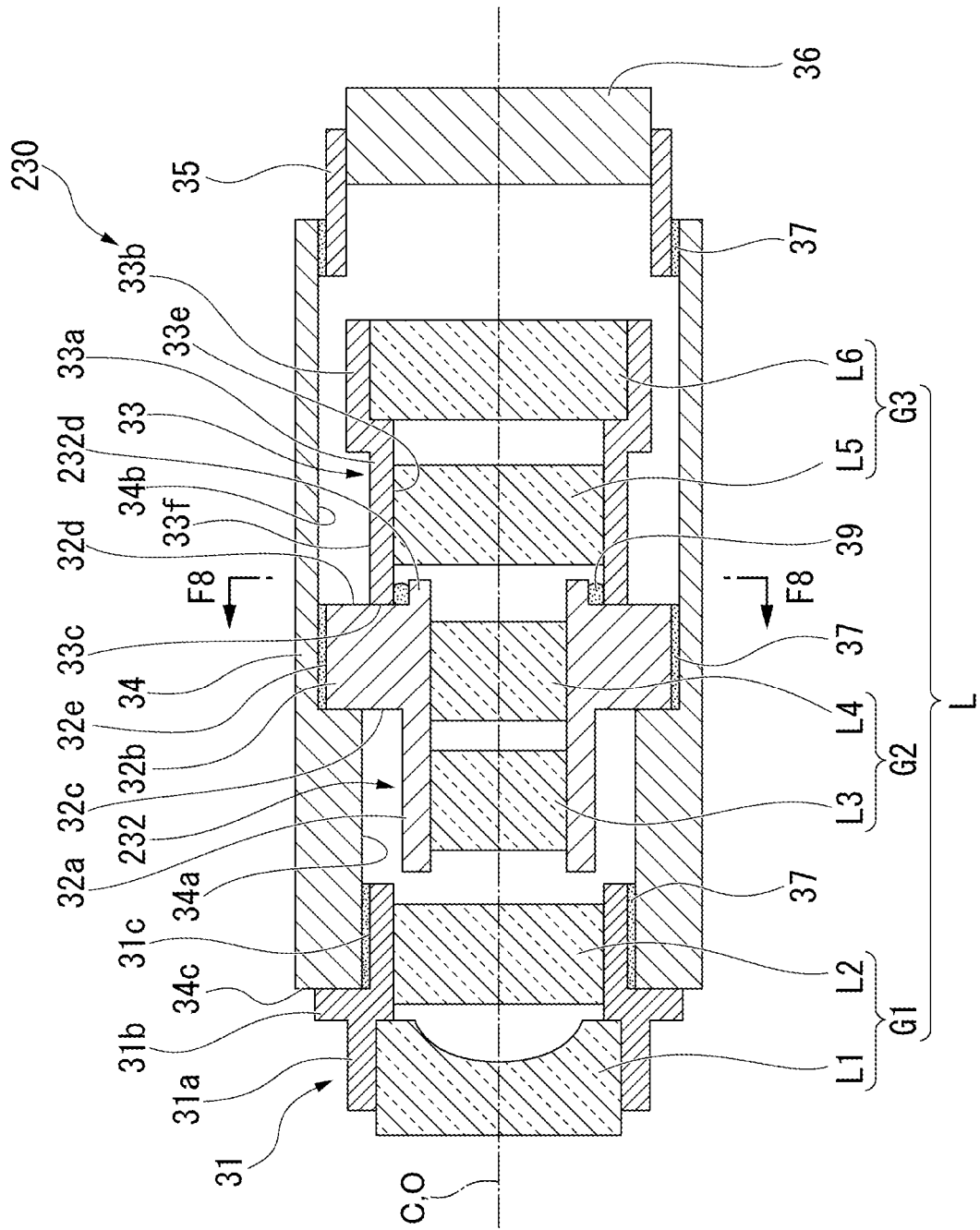
FIG. 7 is a schematic cross-sectional view showing an example of an imaging unit according to a modified example (second modified example) of the first embodiment of the present invention.
Figure 8:
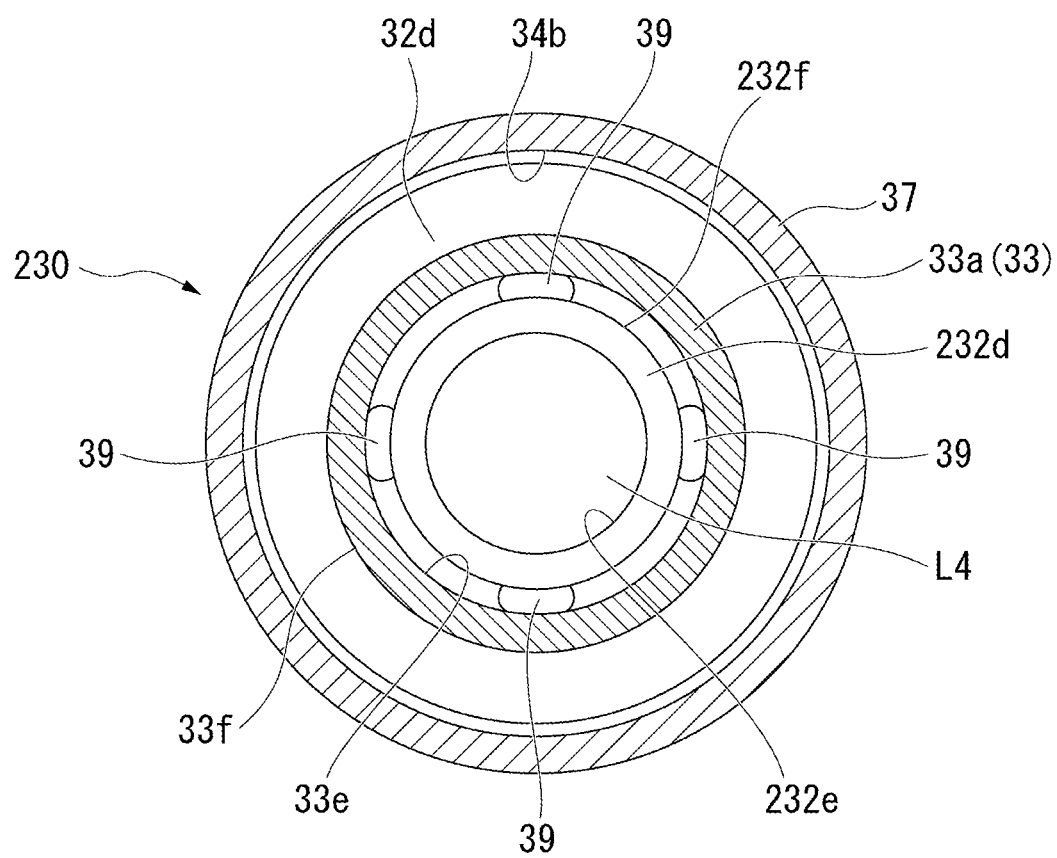
FIG. 8 is a cross-sectional view taken along line F8-F8 in FIG. 7.

FIG. 7 is a schematic cross-sectional view showing an example of an imaging unit according to a modified example (second modified example) of the first embodiment of the present invention. FIG. 8 is a cross-sectional view along line F8-F8 in FIG. 7.

As shown in FIG. 7, an imaging unit 230 (imaging unit of an endoscope) according to this modified example has a second front group lens frame 232 (first lens frame) instead of the second front group lens frame 32 of the imaging unit 30 according to the first embodiment.

As shown in FIG. 1, the imaging unit 230 can be used in place of the imaging unit 30 in the endoscope 2 according to the first embodiment.

The following description will focus on points that differ from the first embodiment.

As shown in FIG. 7, the second front lens group frame 232 is the same as the second front lens group frame 32 except that it further has a protrusion 232d protruding from the second end face 32d of the flange portion 32b of the second front lens group frame 32.

The protrusion 232d protrudes in the axial direction at a position where the first cylindrical portion 33a of the rear lens group frame 33 can be arranged radially outward. The arrangement position of the protrusion 232d in the circumferential direction is not particularly limited as long as it is arranged at a position overlapping the portion to which the adhesive 39 is applied when viewed from the radial direction.

In the example shown in FIG. 8, the protrusion 232d is an annular protrusion formed on the inner peripheral portion of the flange portion 32b when viewed from the axial direction. The diameter of the outer peripheral surface 232f of the protrusion 232d is smaller than the inner diameter of the first cylindrical portion 33a. In the example shown in FIG. 8, the inner peripheral surface 232e of the protrusion 232d is formed by extending the inner peripheral surface of the lens barrel 32a in the axial direction. However, the inner diameter of the protrusion 232d may be larger than the inner diameter of the barrel 32a.

In this modified example, the adhesive 39 is applied along a groove surrounded by the inner peripheral surface 33e, the second end surface 32d, and the outer peripheral surface 232f of the protrusion 232d. For this reason, the adhesive 39 is hardened in a state in which it adheres to the inner peripheral surface 33e and the outer peripheral surface 232f in addition to the corner formed by the inner peripheral surface 33e and the first end surface 32c.

That is, in this modified example, the rear lens group frame 33 is fixed to the protrusion 232d with the adhesive 39 at the portion overlapping the protrusion 232d when viewed in the radial direction.

The imaging unit 230 can be manufactured in substantially the same manner as the imaging unit 30 of the first embodiment except that the second front group lens frame 232 is used instead of the second front group lens frame 32 and the adhesive 39 is applied between the first cylindrical portion 33a and the protrusion 232d.

For example, in this modified example, after the adhesive 39 is applied to the outer peripheral surface 232f of the protrusion 232d, the rear group lens frame 33 is inserted between the second inner peripheral surface 34b and the protrusion 232d.

For example, in this modified example, a thermosetting adhesive may be used as the adhesive 39 because it is difficult to irradiate the adhesive 39 with ultraviolet rays.

According to the imaging unit 230 of this modified example, the rear group lens frame 33 is adhered to the protrusion 232d in the radial direction by hardening the adhesive 39 applied between the first cylindrical portion 33a and the protrusion 232d. As a result, the rear lens group frame 33 is fixed more firmly in the radial direction, so that even if a load is applied to the holder arranged radially outside the objective lens, it becomes easier to maintain the optical performance.

Second Embodiment

An endoscope imaging unit according to a second embodiment of the present invention will be described.

Figure 9:
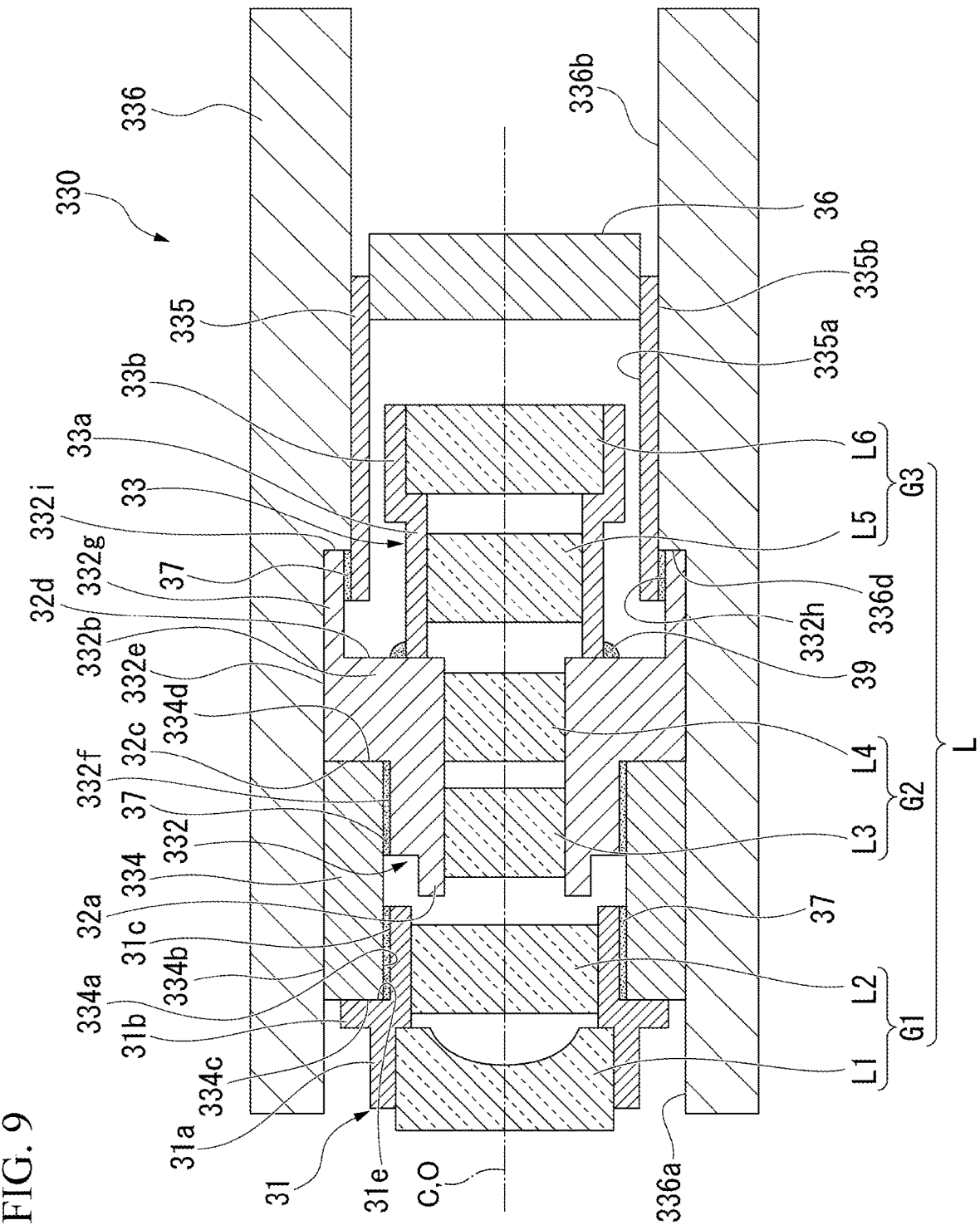
FIG. 9 is a schematic cross-sectional view showing an example of an imaging unit according to a second embodiment of the present invention.

FIG. 9 is a schematic cross-sectional view showing an example of an imaging unit according to the second embodiment of the invention.

As shown in FIG. 9, an imaging unit 330 (imaging unit for an endoscope) according to the present embodiment has a second front group lens frame 332 (first lens frame), an imaging element holding frame 335 (holder), a front side holding frame 334 (holder), and an outer holding frame 336 instead of the second front group lens frame 32, second holding frame 35, and first holding frame 34 of the imaging unit 30 according to the first embodiment.

As shown in FIG. 1, the imaging unit 330 can be used in place of the imaging unit 30 in the endoscope 2 according to the first embodiment.

The following description will focus on points that differ from the first embodiment.

As shown in FIG. 9, the second front lens group frame 332 has a flange portion 332b instead of the flange portion 32b of the second front lens group frame 32 in the first embodiment, and further has an outer circumference fixing portion 332f and a cylindrical portion 332g.

The flange portion 332b is similar to the flange portion 32b except that the diameter of the side surface 332e is equal to the diameter of the outer peripheral surface of the first holding frame 34 in the first embodiment.

The outer peripheral fixing portion 332f is a portion for radially fixing to a front side holding frame 334, which will be described later.

The outer peripheral fixed part 332f is a cylindrical part coaxial with the lens barrel 32a, which is formed to bulge radially outward of the lens barrel 32a. The outer diameter of the outer peripheral fixed portion 332f is larger than the outer diameter of the lens barrel 32a and smaller than the diameter of the first end surface 32c, and is large enough to be inserted into the rear end portion of the front side holding frame 334 described later.

In the example shown in FIG. 9, the outer diameter of the outer peripheral fixing portion 332f is equal to the diameter of the second cylindrical portion 31c of the first front group lens frame 31.

The length of the outer peripheral fixing portion 332f in the axial direction is not particularly limited as long as the necessary fixing strength can be obtained. In the example shown in FIG. 9, it extends to a position closer to the rear end than the front end of the lens barrel 32a, which is closer to the front end than the first end surface 32c. However, the outer peripheral fixing portion 332f may extend to the distal end of the lens barrel 32a. In this case, the outer peripheral fixed portion 332f corresponds to being formed by the outer peripheral surface of the lens barrel that is thicker than the thickness of the lens barrel 32a in the first embodiment.

The cylindrical portion 332g is a portion for fixing an imaging element holding frame 335, which will be described later, in the radial direction.

The cylindrical portion 332g axially protrudes from the second end surface 32d in the outer peripheral portion of the flange portion 332b.

The outer peripheral surface of the cylindrical portion 332g is formed by extending the side surface 332e of the flange portion 332b in the axial direction.

The diameter of the inner peripheral surface 332h of the cylindrical portion 332g is slightly larger than the outer diameter of the imaging element holding frame 335, which will be described later.

The length of the cylindrical portion 332g in the axial direction is shorter than the length of the rear lens group frame 33 in the axial direction.

The imaging element holding frame 335 is the same as the second holding frame 35 in the first embodiment, except that the length in the axial direction is longer. The length of the imaging element holding frame 335 is such that the distal end of the imaging element holding frame 335 can be inserted inside the cylindrical portion 332g of the second front group lens frame 332 when the imaging surface of the imaging element 36 held by the imaging element holding frame 335 is arranged on the image plane of the objective lens L.

The front side holding frame 334 holds the first front group lens frame 31 and the second front group lens frame 332 in a state in which they are positioned with respect to each other in the axial direction and the radial direction.

The shape of the front holding frame 334 is not particularly limited as long as it can hold the first front group lens frame 31 and the second front group lens frame 332.

In the example shown in FIG. 9, it is a cylinder having an inner peripheral surface 334a and an outer peripheral surface 334b coaxial with each other.

The diameter of the inner peripheral surface 334a is equal to the outer diameter of the second cylindrical portion 31c of the first front lens group frame 31 and the diameter of the outer peripheral fixing portion 332f of the second front lens group frame 332.

The diameter of the outer peripheral surface 334b is equal to the diameter of the side surface 332e.

At both ends of the front holding frame 334 in the axial direction, a front-end surface 334c and a rear end surface 334d, which are planes perpendicular to the central axis of the front holding frame 334, are formed.

The distance between the distal end surface 334c and the rear end surface 334d is equal to the distance between the distal end surface 34c and the stepped portion 34d in the first embodiment.

The outer holding frame 336 is a cylinder that holds the outer peripheral portions of the front holding frame 334, the rear group lens frame 33, and the imaging element holding frame 335. The shape of the outer holding frame 336 is not particularly limited as long as it can hold the outer peripheral portions of the front holding frame 334, the rear lens group frame 33, and the imaging element holding frame 335.

In the example shown in FIG. 9, the outer holding frame 336 has a first inner peripheral surface 336a and a second inner peripheral surface 336b in this order along the axial direction.

The first inner peripheral surface 336 a is a cylindrical surface having a diameter slightly larger than the outer diameter of the front holding frame 334 and the diameter of the side surface 332 e of the second front group lens frame 32.

The second inner peripheral surface 336b is a cylindrical surface having a diameter slightly larger than the outer diameter of the imaging element holding frame 335. Therefore, a stepped portion 336d is formed between the first inner peripheral surface 336a and the second inner peripheral surface 336b.

The stepped portion 336d is a plane perpendicular to the central axis of the first inner peripheral surface 336a. The stepped portion 336d is used for positioning the second front group lens frame 32 in the axial direction by abutting the end surface 332i of the cylindrical portion 332g of the second front group lens frame 332.

The rear lens group frame 33 in the imaging unit 330 of this embodiment is fixed to the second end surface 32d of the second front lens group frame 332 with an adhesive 39 in the same manner as in the first embodiment.

An imaging element holding frame 335 to which an imaging element 36 is fixed is fixed to an inner peripheral surface 332h of a cylindrical portion 332g with an adhesive 37 interposed therebetween, as in the first embodiment.

In the imaging unit 330 of the present embodiment, the end surface 31e of the first front lens group frame 31 abuts the distal end surface 334c of the front holding frame 334 in the axial direction, and is fixed to the inner peripheral surface 334a of the front holding frame 334 with the adhesive 37 interposed in the radial direction.

The second front group lens frame 332 is fixed to the inner peripheral surface 334a of the front holding frame 334 with the first end surface 32c in contact with the rear end surface 334d of the front holding frame 334 in the axial direction and the adhesive 37 interposed in the radial direction.

In the outer holding frame 336, the front side holding frame 334 and the second front group lens frame 332 are inserted into the first inner peripheral surface 336a, and the outer peripheral surface 335b of the imaging element holding frame 335 is inserted into the second inner peripheral surface 336b, with the end surface 332i of the cylindrical portion 332g of the second front group lens frame 332 in contact with the stepped portion 336d.

The outer holding frame 336 is in contact with and fixed to at least one of the front holding frame 334, the second front group lens frame 332, and the imaging element holding frame 335 while the front holding frame 334, the second front group lens frame 332, and the imaging element holding frame 335 are inserted inside.

The fixing method of the member fixed to the outer holding frame 336 is not particularly limited. As a method for fixing the member fixed to the outer holding frame 336, for example, adhesion, screw fastening, or the like may be used.

An example of a method for manufacturing such an imaging unit 330 will be described, focusing on points that differ from the first embodiment.

FIGS. 10A and 10B are schematic cross-sectional views showing an example of a method for manufacturing an imaging unit according to the second embodiment of the present invention.

To manufacture the imaging unit 330, the first front group lens frame 31 to which L1-L2 are fixed, the second front group lens frame 332 to which the lenses L3-L4 are fixed, the rear group lens frame 33 to which the lenses L5-L6 are fixed, and the imaging device holding frame 335 to which the imaging device 36 is fixed are formed in the same manner as in the first embodiment.

Figure 10:
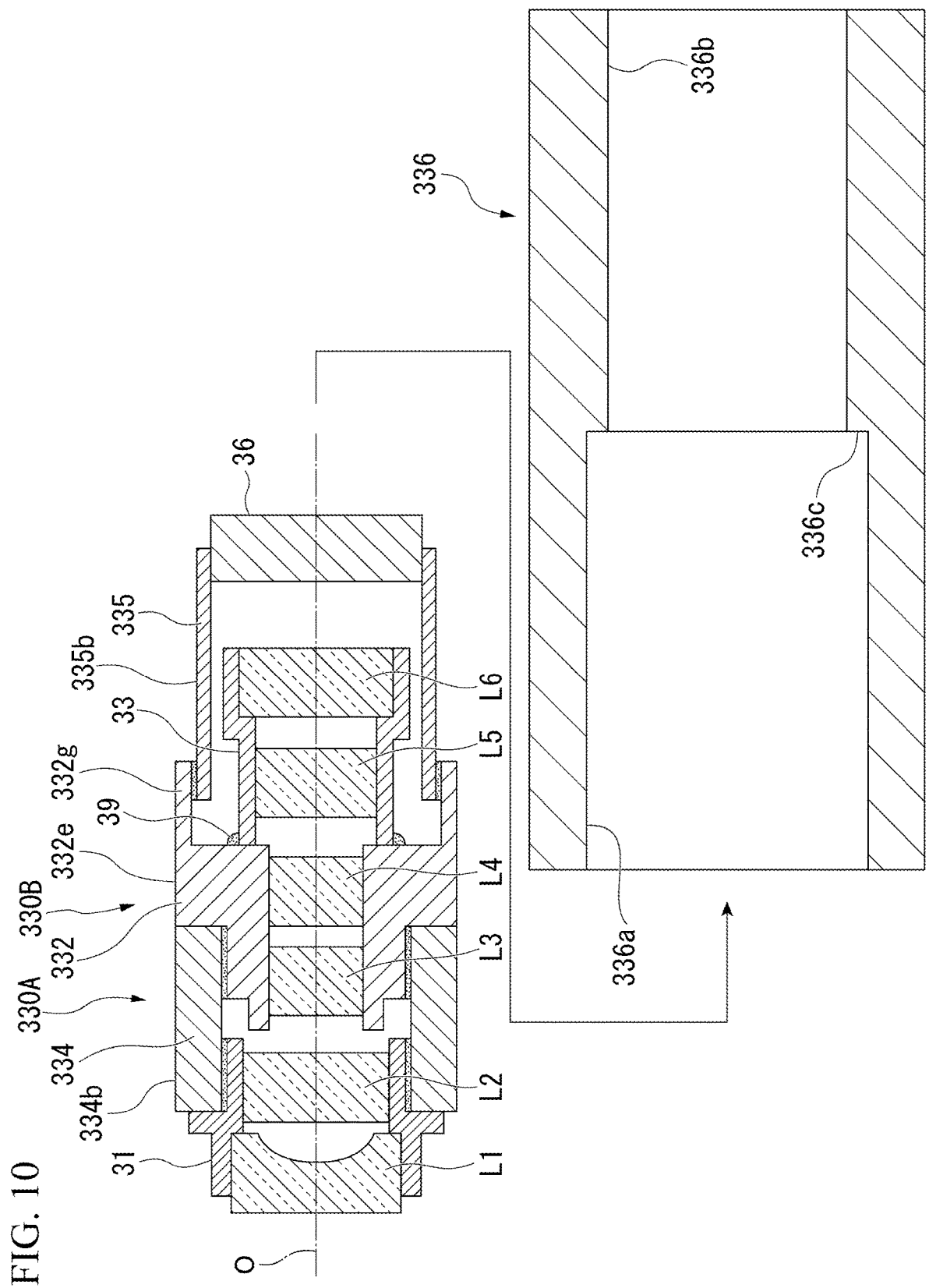
FIG. 10 is a schematic cross-sectional view showing an example of a method for manufacturing an imaging unit according to the second embodiment of the present invention.

As shown in FIG. 10, the first front group lens frame 31 and the second front group lens frame 332 are fixed to the front holding frame 334 to form a first assembly 330A.

Thereafter, the position of the rear lens group frame 33 is adjusted for the first assembly 330A in the same manner as in the first embodiment, and the rear lens group frame 33 is fixed to the second front lens group frame 332 with the adhesive 39.

In this embodiment, the cylindrical portion 332g protrudes from the first end surface 32c, but the cylindrical portion 332g is shorter than the first cylindrical portion 33a. This facilitates the application and curing of the adhesive 39 on the second end face 32d.

After that, similarly to the first embodiment, the imaging element holding frame 335 is fixed to the inner peripheral surface of the cylindrical portion 332g.

In this way, the second assembly 330B including the objective lens L with well-adjusted imaging performance on the image plane is formed.

After that, the second assembly 330B is inserted into the outer holding frame 336 from the distal end side where the first inner peripheral surface 336a is formed, and the second assembly 330B is fixed to the outer holding frame 336. Thereby, the imaging unit 330 as shown in FIG. 9 is manufactured.

The imaging unit 330 of this embodiment described above is an imaging unit of an endoscope that is arranged and used at the distal end portion 6 of the endoscope 2.

The imaging unit 330 has the same objective lens L and imaging element 36 as in the first embodiment. The second front group lens frame 332 in this embodiment is an example of a first lens frame that holds the first lens.

The outer holding frame 336, the front holding frame 334, and the imaging element holding frame 335 house the first lens frame and the second lens frame inside, and are examples of holders that hold the first lens frame.

In the imaging unit 330, the second lens frame is fixed to the first lens frame without contacting the imaging element 36 and the holder and with a gap between the imaging element 36 and the holder.

In the imaging unit 330, the rear lens group frame 33 is fixed to the second front lens group frame 332, and is arranged inside the holder while being separated from the imaging element 36 and the holder. As a result, as in the first embodiment, the fixed portion formed by the adhesive 39 is prevented from being displaced or damaged, so that the optical performance of the objective lens L adjusted when the rear group lens frame 33 is fixed is maintained. Furthermore, even if an external force acts on the imaging element 36 or the imaging element 36 is deformed by heat, the fixed portion formed by the adhesive 39 is prevented from being displaced or damaged.

According to this embodiment, the second assembly 330B can be formed by forming the first assembly 330A, adjusting the position of the rear lens group frame 33 with respect to the first assembly 330A, and fixing the rear lens group frame 33 without the outer holding frame 336 being attached. Thereafter, when the second assembly 330B is fixed to the outer holding frame 336, there is no need to adjust the positions of the objective lens L and the imaging element 36, which facilitates assembly.

As described above, according to the imaging unit 330 of the present embodiment and the endoscope 2 in which the imaging unit 330 is arranged at the distal end portion 6, it is easy to maintain the optical performance even if a load is applied to the holder arranged radially outward of the objective lens.

[Third Modification]

An imaging unit of an endoscope according to a modified example (third modified example) of the second embodiment of the present invention will be described.

Figure 11:
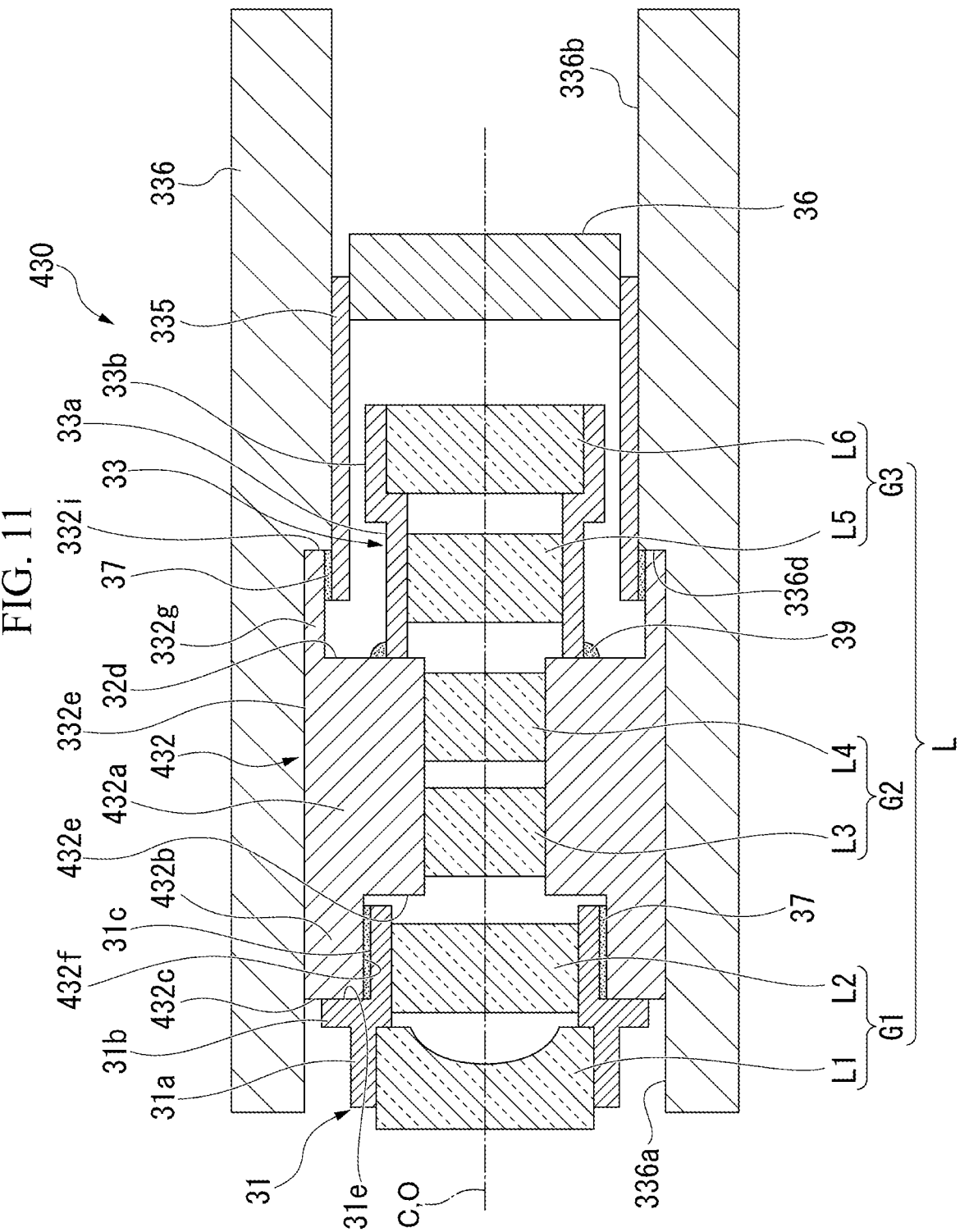
FIG. 11 is a schematic cross-sectional view showing an example of an imaging unit according to a modified example (third modified example) of the second embodiment of the present invention.

FIG. 11 is a schematic cross-sectional view showing an example of an imaging unit according to a modified example (third modified example) of the second embodiment of the present invention. FIG. 6 is a cross-sectional view taken along line F6-F6 in FIG. 5.

As shown in FIG. 11, an imaging unit 430 (endoscope imaging unit) according to the present modification has a second front group lens frame 432 (first lens frame) instead of the second front group lens frame 332 and the front side holding frame 334 of the imaging unit 330 according to the second embodiment.

As shown in FIG. 1, the imaging unit 430 can be used in place of the imaging unit 30 in the endoscope 2 according to the first embodiment.

The following description will focus on points that differ from the second embodiment.

As shown in FIG. 11, the second front group lens frame 432 has a shape corresponding to the fact that the second front group lens frame 332 and the front side holding frame 334 in the second embodiment are integrated at their contact portions and fixed portions.

The second front group lens frame 432 has a barrel 432a, a cylindrical portion 332g, and a front cylindrical portion 432b.

The lens barrel 432a is a cylindrical portion obtained by increasing the thickness of the lens barrel 32a in the second embodiment in the radial direction to the side surface 332e. The lens barrel 432a has a first end face 432e on the front-end side and a second end face 32d similar to the lens barrel 32a on the rear end side.

The length of the lens barrel 432a in the axial direction is not particularly limited as long as it can hold the second front lens group G2 and does not come into contact with the second cylindrical portion 31c of the first front lens group frame 31 during assembly.

A cylindrical portion 332g in this modified example is formed in the same manner as in the second embodiment except that it protrudes from the second end surface 32d of the lens barrel 432a.

The front cylindrical portion 432b is a cylindrical portion protruding from the first end face 432e of the lens barrel 432a to the same position as the distal end face 334c of the front holding frame 334 in the second embodiment.

A distal end surface 432c of the lens barrel 432a is a plane perpendicular to the central axis of the lens barrel 432a. Like the distal end surface 334c, the distal end surface 432c is used to position the first front lens group frame 31 in the axial direction by bringing the end surface 31e of the first front lens group frame 31 into contact therewith.

The rear lens group frame 33 in the imaging unit 430 of this embodiment is fixed to the second end surface 32d of the second front lens group frame 432 with an adhesive 39 in the same manner as in the second embodiment.

The first front lens group frame 31 in the imaging unit 430 of the present embodiment is fixed to the inner peripheral surface 334a of the front holding frame 334 with the end surface 31e axially abutting the front-end surface 432c of the front cylindrical portion 432b of the second front lens group frame 432, and with the adhesive 37 interposed in the radial direction.

The second front lens group frame 332 is fixed to the inner peripheral surface 432f of the front cylindrical portion 432b of the second front lens group frame 432 with the first end surface 32c in axial contact with the rear end surface 334d of the front holding frame 334 and the adhesive 37 interposed in the radial direction.

In the outer holding frame 336 in this embodiment, the front side holding frame 334 and the second front group lens frame 332 are inserted into the first inner peripheral surface 336a, and the outer peripheral surface 335b of the imaging element holding frame 335 is inserted into the second inner peripheral surface 336b, with the end surface 332i of the cylindrical portion 332g of the second front group lens frame 432 in contact with the stepped portion 336d.

The outer holding frame 336 is in contact with the second front group lens frame 432 and the imaging element holding frame 335 while the second front group lens frame 432 and the imaging element holding frame 335 are inserted inside, and is fixed to at least one of them as in the second embodiment.

The imaging unit 430 can be manufactured in the same manner as in the second embodiment, except that the second front lens group frame 432 is used instead of the front holding frame 334 and the second front lens group frame 332.

The imaging unit 430 of this embodiment described above is an imaging unit of an endoscope that is arranged and used at the distal end portion 6 of the endoscope 2.

The imaging unit 430 has the same objective lens L and imaging element 36 as in the second embodiment. The second front group lens frame 432 in this embodiment is an example of a first lens frame that holds the first lens.

The outer holding frame 336 and the imaging element holding frame 335 are examples of holders that house the first lens frame and the second lens frame as a whole and hold the first lens frame.

In the imaging unit 430, the second lens frame is fixed to the first lens frame without contacting the imaging element 36 and the holder and with a gap between the imaging element 36 and the holder.

The imaging unit 430 has the same configuration as the first holding frame 34 and the second front group lens frame 332 integrated in the second embodiment, and thus has the same function as the imaging unit 330.

As described above, according to the imaging unit 430 of the present embodiment and the endoscope 2 in which the imaging unit 430 is arranged at the distal end portion 6, it is easy to maintain the optical performance even if a load is applied to the holder arranged radially outside the objective lens.

Third Embodiment

An endoscope imaging unit according to a third embodiment of the present invention will be described.

Figure 12:
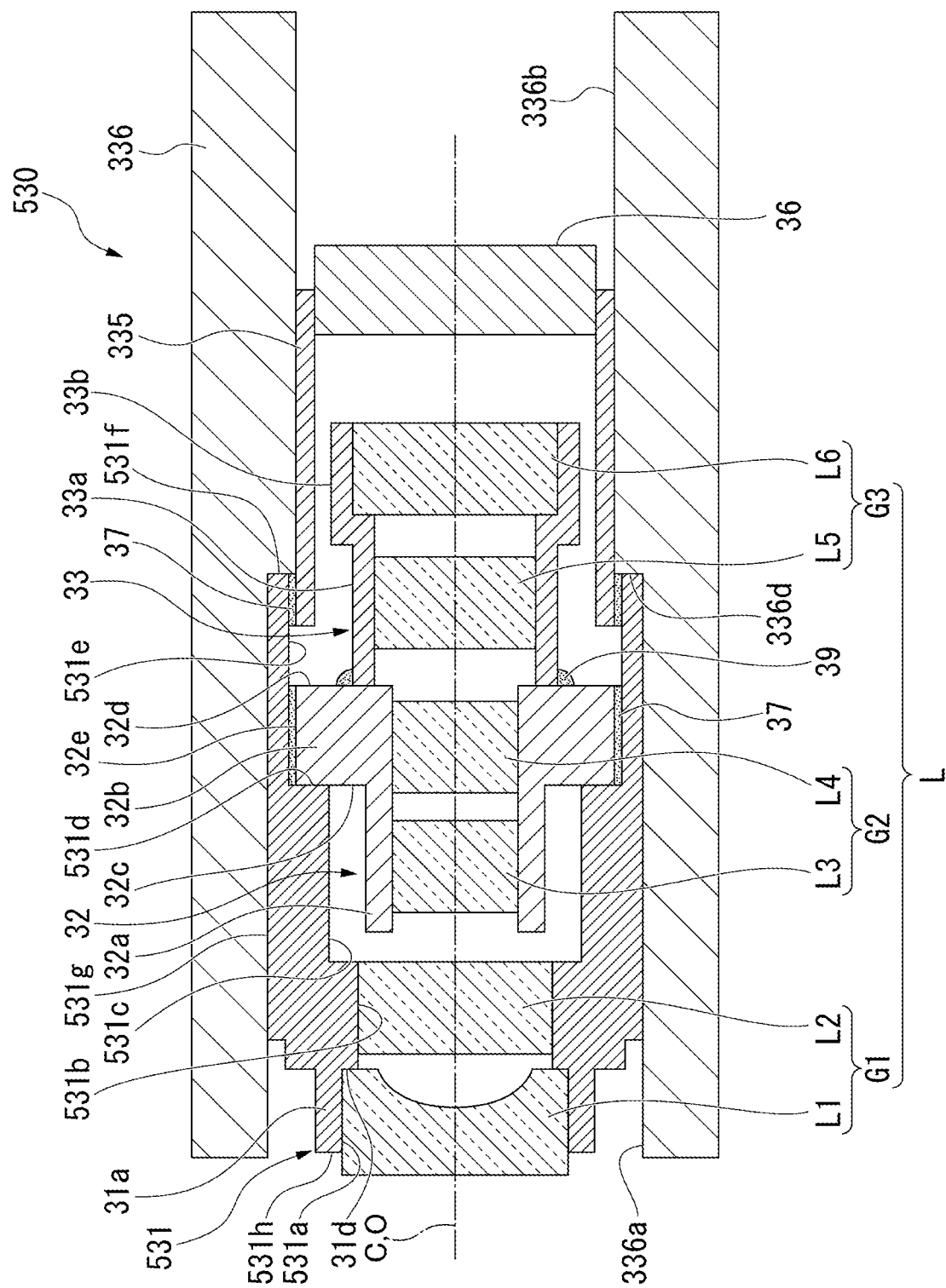
FIG. 12 is a schematic cross-sectional view showing an example of an imaging unit according to a third embodiment of the present invention.

FIG. 12 is a schematic cross-sectional view showing an example of an imaging unit according to the third embodiment of the invention.

As shown in FIG. 12, an imaging unit 530 (imaging unit of an endoscope) according to the present embodiment has a first front group lens frame 531 (holder) instead of the first front group lens frame 31 and the front side holding frame 334 of the imaging unit 330 according to the second embodiment, and has a second front group lens frame 32 (first lens frame) similar to that of the first embodiment instead of the second front group lens frame 432.

As shown in FIG. 1, the imaging unit 530 can be used in place of the imaging unit 30 in the endoscope 2 according to the first embodiment.

The following description will focus on points that differ from the first and second embodiments.

As shown in FIG. 12, the first front lens group frame 531 holds the first front lens group G1 and accommodates and holds the second front lens group frame 32 inside. The shape of the first front group lens frame 531 is substantially cylindrical.

The axial distance from the front-end surface 531h to the rear end surface 531f of the first front lens group frame 531 is equal to the distance from the front-end surface of the first front lens group frame 31 to the end surface 332i of the second front lens group frame 332 in the first embodiment.

A front-end surface 531h and a rear end surface 531f are planes orthogonal to the center axis of the first front group lens frame 531.

A cylindrical outer peripheral surface 531g having the same diameter as the side surface 332e of the second front lens group frame 32 in the second embodiment is formed on the outermost peripheral portion of the first front lens group frame 531. The outer peripheral surface 531g extends over substantially the entire length of the first front lens group frame 531 in the axial direction except for the distal end portion thereof.

A first inner peripheral surface 531a, a second inner peripheral surface 531b, a third inner peripheral surface 531c, and a fourth inner peripheral surface 531e are formed in this order from the front-end surface 531h to the rear end surface 531f on the inner peripheral portion of the first front group lens frame 531.

The first inner peripheral surface 531a holds the first lens L1. The first inner peripheral surface 531a is a cylindrical surface similar to the inner peripheral surface of the first cylindrical portion 31a of the first front group lens frame 31.

The second inner peripheral surface 531b holds the second lens L2. The second inner peripheral surface 531b is a cylindrical surface similar to the inner peripheral surface of the second cylindrical portion 31c of the first front lens group frame 31.

A stepped portion 31d similar to that of the first embodiment is formed between the first inner peripheral surface 531a and the second inner peripheral surface 531b.

The stepped portion 31d of this embodiment is used for positioning the first lens L1 in the axial direction, as in the first embodiment.

The third inner peripheral surface 531c is a cylindrical surface having a diameter larger than the outer diameter of the lens barrel 32a of the second front group lens frame 32 and smaller than the side surface 32e of the flange portion 32b.

The fourth inner peripheral surface 531e is a cylindrical surface having the same diameter as the second inner peripheral surface 34b of the first holding frame 34 in the first embodiment. The fourth inner peripheral surface 531e is used for fixing the imaging element holding frame 335, like the inner peripheral surface of the cylindrical portion 332g of the second front group lens frame 332 in the second embodiment.

Between the third inner peripheral surface 531c and the fourth inner peripheral surface 531e, a stepped portion 531d consisting of a plane perpendicular to the central axis of the first front group lens frame 531 is formed.

The first end surface 32c of the flange portion 32b of the second front group lens frame 32 abuts against the stepped portion 531d. The stepped portion 531d is used for positioning the second front group lens frame 32 in the axial direction.

The first front group lens frame 531 has a shape corresponding to that the first front group lens frame 31 and the first holding frame 34 in the first embodiment are integrated at their abutting portions and fixed portions, except that the length in the axial direction is short.

The rear end surface 531f of the first front lens group frame 531 is located on the front-end side of the rear end portion of the rear lens group frame 33.

The second front lens group frame 32 in the imaging unit 530 of the present embodiment is fixed to the fourth inner peripheral surface 531e with the first end surface 32c in contact with the stepped portion 531d of the first front lens group frame 531 in the axial direction and with the adhesive 37 interposed in the radial direction.

The rear lens group frame 33 in the imaging unit 530 of this embodiment is fixed to the second end surface 32d of the second front lens group frame 32 with an adhesive 39 in the same manner as in the first embodiment.

The second holding frame 35 in the imaging unit 530 of this embodiment is fixed to the first front group lens frame 531 in the same manner as in the second embodiment, except that it is fixed to the fourth inner peripheral surface 531e of the first front group lens frame 531 with an adhesive 37 interposed therebetween.

The outer holding frame 336 in the imaging unit 530 of this embodiment is in contact with the first front group lens frame 531 and the imaging element holding frame 335 in a state in which the first front group lens frame 531 and the imaging element holding frame 335 are inserted inside, and is fixed to at least one of these in the same manner as in the second embodiment.

The imaging unit 530 can be manufactured in the same manner as in the second embodiment, except that the first front group lens frame 531 and the second front group lens frame 32 are used instead of the first front group lens frame 31, the front side holding frame 334, and the second front group lens frame 432.

The imaging unit 530 according to the present embodiment described above is an imaging unit of an endoscope that is arranged and used at the distal end portion 6 of the endoscope 2.

The imaging unit 530 has the same objective lens L and imaging element 36 as in the second embodiment. The first front group lens frame 531, the second holding frame 35, and the outer holding frame 336 in the present embodiment accommodate the first lens frame and the second lens frame inside, and are examples of holders that hold the first lens frame.

In the imaging unit 530, the second lens frame is fixed to the first lens frame without contacting the imaging element 36 and the holder and with a gap between the imaging element 36 and the holder.

The imaging unit 530 of the present embodiment can be said to correspond to a configuration in which the first front lens group frame 31 and the first holding frame 34 in the first embodiment are integrated at their contact portions and fixed portions and inserted inside the outer holding frame 336, except that the fixed position of the image sensor holding frame 335 overlaps with the rear lens group frame 33 when viewed in the radial direction.

Although the imaging unit 530 differs from the first and second embodiments in the configuration of the holder, the configuration in which the first lens frame to which the second lens frame is fixed is accommodated inside the holder and the first lens frame is fixed to the holder is the same. Therefore, it has the same function as the imaging units 30 and 330.

As described above, according to the imaging unit 530 of the present embodiment and the endoscope 2 having the imaging unit 530 arranged at the distal end portion 6, it is easy to maintain the optical performance even if a load is applied to the holder arranged radially outside the objective lens.

Fourth Embodiment

An endoscope imaging unit according to a fourth embodiment of the present invention will be described.

Figure 13:
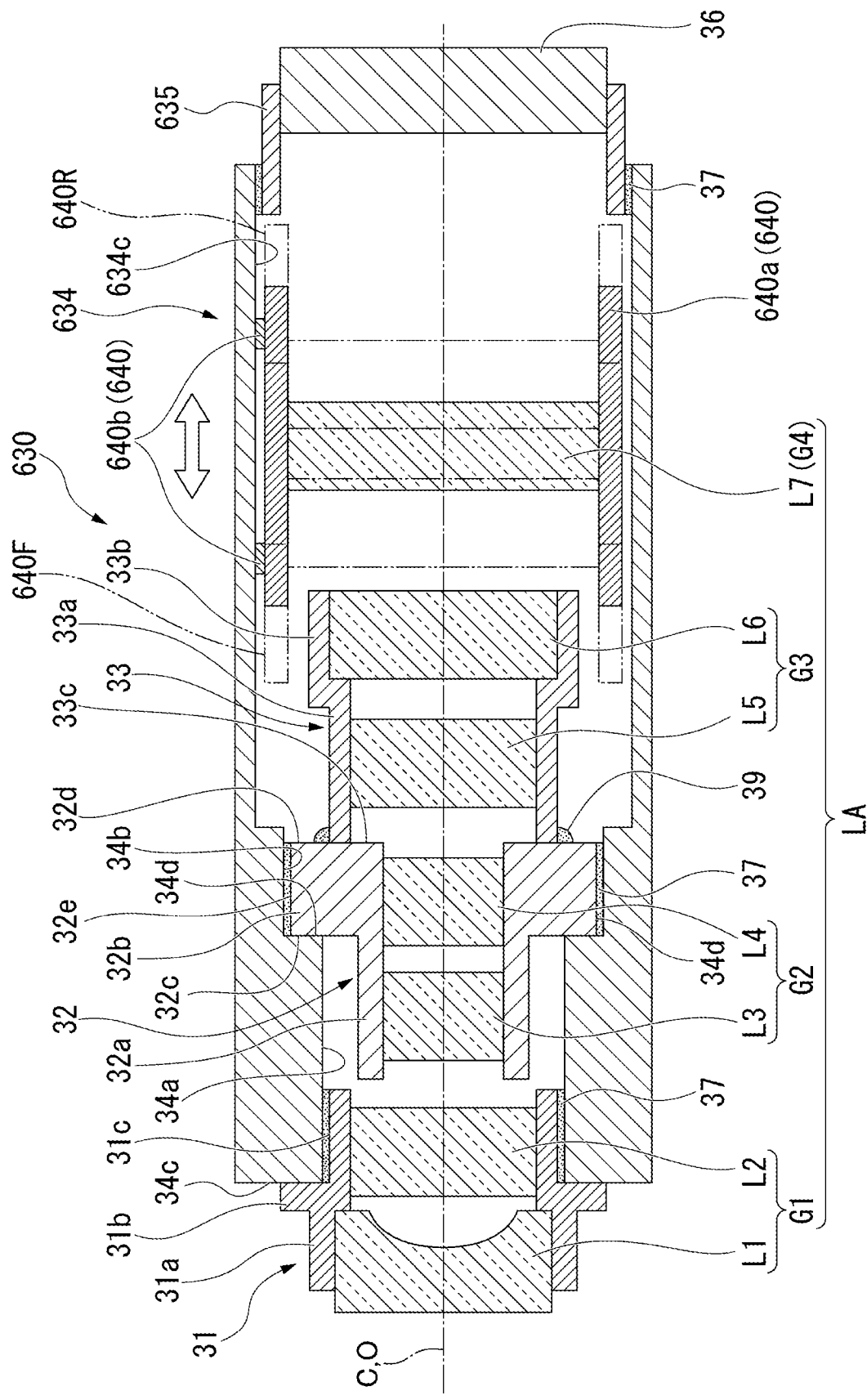
FIG. 13 is a schematic cross-sectional view showing an example of an imaging unit according to a fourth embodiment of the present invention.

FIG. 13 is a schematic cross-sectional view showing an example of an imaging unit according to the fourth embodiment of the invention.

As shown in FIG. 13, an imaging unit 630 (imaging unit of an endoscope) according to the present embodiment has an objective lens LA, a first holding frame 634 (holder) and a second holding frame 635 (holder) instead of the objective lens L, first holding frame 34 and second holding frame 35 of the imaging unit 30 according to the first embodiment. The imaging unit 630 further has an actuator 640 inside the first holding frame 634.

As shown in FIG. 1, the imaging unit 630 can be used instead of the imaging unit 30 in the endoscope 2 according to the first embodiment.

The following description will focus on points that differ from the first embodiment.

As shown in FIG. 13, the objective lens LA has a moving lens G4 in addition to the first front lens group G1, second front lens group G2, and rear lens group G3 in the first embodiment.

The moving lens G4 is held movably in the direction along the optical axis O of the objective lens LA by an actuator 640, which will be described later. For example, the moving lens G4 may be used for focus adjustment, magnification adjustment, zoom variation, etc. in the imaging unit 630.

The lens configuration and arrangement position of the moving lens G4 are set according to the functions required of the moving lens G4. In the example shown in FIG. 13, the moving lens G4 is composed of the seventh lens L7, and is arranged between the rear lens group G3 and the imaging element 36 so as to be movable in the optical axis direction. The shape of each optical surface of the seventh lens L7 in FIG. 13 is drawn as a planar shape for simplicity, but like the lenses L2 to L6, it is formed in any of convex, concave, and planar shapes so that the necessary refractive power of the objective lens LA can be obtained.

The first holding frame 634 is a cylindrical body longer than the first holding frame 34 in the first embodiment. The first holding frame 634 has a distal end surface 34c, a first inner peripheral surface 34a, a stepped portion 34d, and a second inner peripheral surface 34b, like the first holding frame 34 in the first embodiment.

On the inner peripheral portion of the first holding frame 634, a third inner peripheral surface 634c consisting of a cylindrical surface coaxial with the second inner peripheral surface 34b and having a large diameter extends from a position on the image side of the first end surface 32c of the flange portion 32b of the second front group lens frame 32 to the rear end.

An actuator 640, which will be described later, is arranged inside the third inner peripheral surface 634c.

The second holding frame 635 is a tubular body similar to the second holding frame 35 in the first embodiment, except that it is fixed to the third inner peripheral surface 634c of the first holding frame 634 with an adhesive 37 interposed. The inner peripheral surface of the second holding frame 635 may have an uneven shape necessary for positioning and holding the imaging element 36.

The actuator 640 has a moving frame 640a that holds the moving lens G4 and a moving mechanism 640b that moves the moving frame 640a with respect to the first holding frame 634 in the optical axis direction.

The shape of the moving frame 640a is not particularly limited as long as it has a cylindrical shape capable of holding the moving lens G4. In the example shown in FIG. 13, the moving frame 640a has a cylindrical shape with a smaller diameter than the third inner peripheral surface 634c and a larger diameter than the outer diameter of the rear lens group frame 33.

The configuration of the moving mechanism 640b is not particularly limited as long as it can move the actuator 640 in the optical axis direction. For example, a mechanism including permanent magnets and coils may be used.

The coil of the moving mechanism 640b is communicably connected to the operation portion 10 (see FIG. 1) by an electric cable inside the insertion portion 9. For example, the operator can operate the movement amount and movement direction of the moving frame 640a by operating the operating lever 24 or the switch portion 23 shown in FIG. 1.

With this configuration, the first front group lens frame 31 and the second front group lens frame 32 are fixed to the first holding frame 634 in the same manner as in the first embodiment. The rear lens group frame 33 is fixed to the second end face 32d of the second front lens group frame 32 with an adhesive 39 in the same manner as in the first embodiment.

The second holding frame 635 holding the imaging element 36 is fixed to the third inner peripheral surface 634c of the first holding frame 634 with the adhesive 37 interposed.

Inside the first holding frame 634, an actuator 640 holding the moving lens G4 is arranged between the rear lens group frame 33, the second holding frame 35, and the imaging element.

The actuator 640 can move the moving lens G4 to the position closest to the object within the moving range of the moving lens G4. In this case, the actuator 640 moves closer to the object side than the second holding frame 635 and reaches the position of the actuator 640F indicated by the two-dot chain line. At this time, the moving frame 640a is positioned radially outward of the second cylindrical portion 33b, and neither the actuator 640F nor the moving lens G4 come into contact with the rear lens group frame 33 and the rear lens group G3.

The actuator 640 can move to the position closest to the image side of the moving lens G4 within the moving range of the moving lens G4. In this case, the actuator 640 moves toward the image side so that the distance from the rear lens group frame 33 increases, and moves to the position of the actuator 640R indicated by the two-dot chain line. At this time, the moving frame 640*a* stops without coming into contact with either the second holding frame 635 or the imaging element 36.

The imaging unit 630 according to the present embodiment described above is an imaging unit of an endoscope that is arranged and used at the distal end portion 6 of the endoscope 2.

The imaging unit 630 has an objective lens LA and an imaging element 36. The first holding frame 634 and the second holding frame 635 in the present embodiment house the first lens frame and the second lens frame inside, and are examples of holders that hold the first lens frame.

In the imaging unit 630, the second lens frame is fixed to the first lens frame without contacting the imaging element 36 and the holder and with a gap between the imaging element 36 and the holder.

The imaging unit 630 of this embodiment differs from the first embodiment in that it has a moving lens G4 included in the objective lens LA between the rear lens group G3 and the imaging element. Therefore, the imaging unit 630 has the same function as the imaging unit 30 of the first embodiment.

In this embodiment, when the moving lens G4 is moved in the optical axis direction by the actuator 640, the rear group lens frame 33 is accommodated inside the holder without contacting the actuator 640 and the moving lens G4.

Therefore, even if a load that deforms the holder due to external force, heat, or the like is applied to the holder, the load received by the holder will not be transmitted to the second lens frame through the actuator 640 and the movable lens G4.

As described above, according to the imaging unit 630 of the present embodiment and the endoscope 2 in which the imaging unit 630 is arranged at the distal end portion 6, it is easy to maintain the optical performance even if a load is applied to the holder arranged radially outward of the objective lens.

Fifth Embodiment

An endoscope imaging unit according to a fifth embodiment of the present invention will be described.

Figure 14:
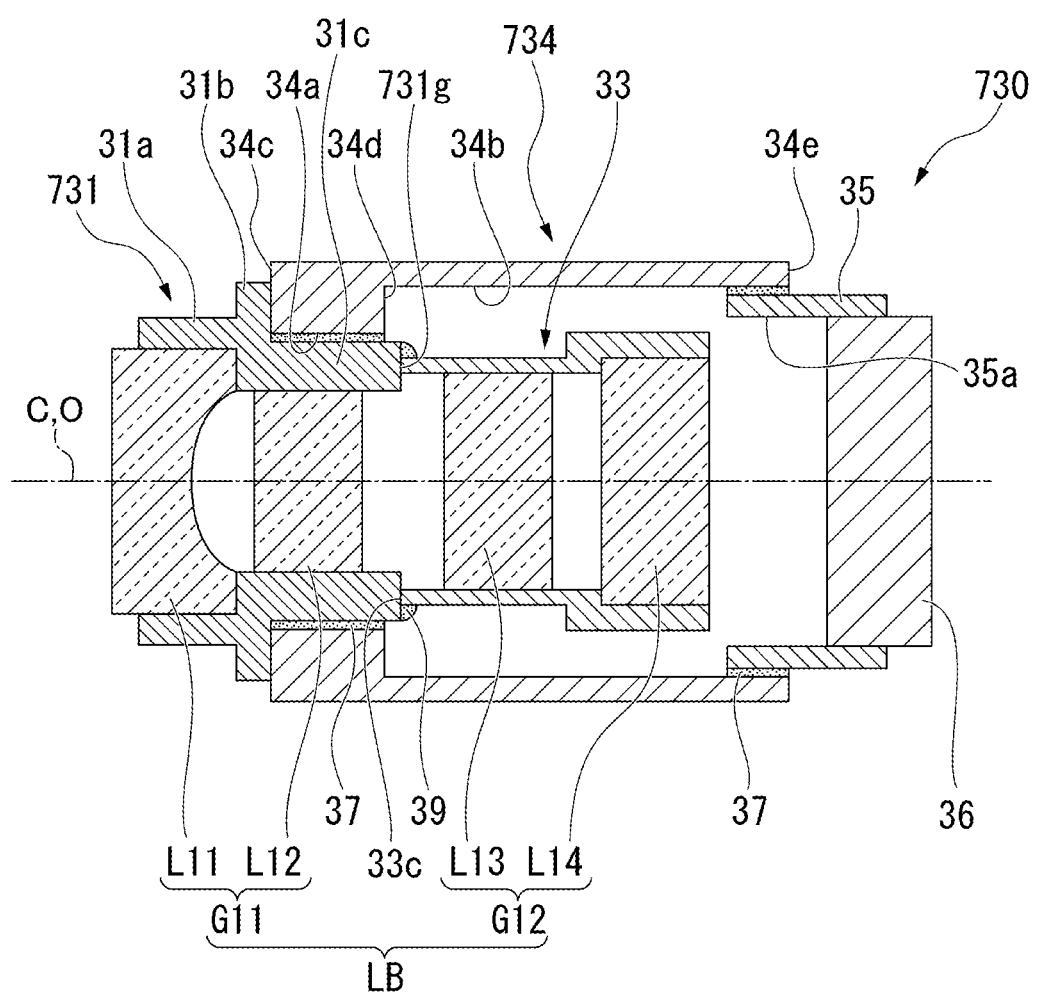
FIG. 14 is a schematic cross-sectional view showing an example of an imaging unit according to a fifth embodiment of the present invention.

FIG. 14 is a schematic cross-sectional view showing an example of an imaging unit according to the fifth embodiment of the invention.

As shown in FIG. 14, an imaging unit 730 (imaging unit for an endoscope) according to the present embodiment has a front lens group G11 (first lens) and a rear lens group G12 (second lens) instead of the first front lens group G1, second front lens group G2, and rear lens group G3 of the imaging unit 30 according to the first embodiment. The front lens group G11 and the rear lens group G12 constitute an objective lens LB in the imaging unit 730.

Accordingly, in the imaging unit 730, the second front group lens frame 32 of the imaging unit 30 is removed, and instead of the first front group lens frame 31 and first holding frame 34 of the imaging unit 30, a front group lens frame 731 (first lens frame) and a first holding frame 734 (holder) are provided.

As shown in FIG. 1, the imaging unit 730 can be used instead of the imaging unit 30 in the endoscope 2 according to the first embodiment.

The following description will focus on points that differ from the first embodiment.

As shown in FIG. 14, the front lens group G11 consists of a first lens L11 and a second lens L12. The rear lens group G12 is composed of a third lens L13 and a fourth lens L14.

The configuration of the lenses L11-L14 is not particularly limited as long as the optical characteristics required for the objective lens LB are obtained.

The front lens group frame 731 is the same as the first front lens group frame 31, except that it holds the first lens L11 and the second lens L12 instead of the first lens L1 and the second lens L2, and that an end face 731*g* with which the end face 33*c* of the rear lens group frame 33 can come into contact is formed at the end of the second cylindrical portion 31*c* on the image side.

The end face 731*g* is a plane perpendicular to the central axis of the front lens group frame 731. The end face 731*g* has a width that allows the end face 33*c* to move in the radial direction and to allow the adhesive 39 to be applied.

The rear lens group frame 33 in this embodiment holds the third lens L13 and the fourth lens L14 instead of the fifth lens L5 and the sixth lens L6.

The rear lens group frame 33 is fixed to an end surface 731*g* of the front lens group frame 731 with an adhesive 39 as in the first embodiment.

The first holding frame 734 is the same as the first holding frame 34, except that the length of the first inner peripheral surface 34*a* is shorter than that of the second cylindrical portion 31*c* of the front lens group frame 731, and that the second inner peripheral surface 34*b* extends further toward the image side than the image-side end of the rear lens group frame 33 fixed to the front lens group frame 731.

The second holding frame 35 and the imaging element 36 in this embodiment are fixed to the second inner peripheral surface 34*b* of the first holding frame 734 in the same manner as in the first embodiment.

With such a configuration, the first holding frame 734 of the imaging unit 730 accommodates the second cylindrical portion 31*c* on the image side of the flange portion 31*b* in the front lens group frame 731 and the entire rear lens group frame 33 inside.

The image formed by the objective lens LB is picked up by the imaging element 36.

The imaging unit 730 according to the present embodiment described above is an imaging unit of an endoscope that is arranged and used at the distal end portion 6 of the endoscope 2.

The front lens group G11 and the rear lens group G12 are examples of a first lens and a second lens included in the objective lens LB.

The front group lens frame 731 is an example of a first lens frame that holds the first lens.

The rear group lens frame 33 is an example of a second lens frame that is fixed to the first lens frame and holds the second lens.

The first holding frame 734 and the second holding frame 35 fixed to the first holding frame 734 house part of the first lens frame and the second lens frame inside, and are an example of a holder that holds the first lens frame.

In the imaging unit 730, the second lens frame is fixed to the first lens frame without contacting the imaging element 36 and the holder and with a gap between the imaging element 36 and the holder.

According to the imaging unit 730 of the present embodiment, the rear lens group frame 33 is housed inside the first holding frame 734, and a part of the front lens group frame 731 including the adhesively fixed portion to the rear lens group frame 33 is housed inside the holder.

In particular, as in the first embodiment, the rear lens group frame 33 is also spaced apart from the imaging device 36 fixed to the holder, is not in contact with the imaging device 36, and is arranged with a gap with respect to the imaging device 36.

As a result, as in the first embodiment, the optical performance such as the imaging performance of the objective lens LB adjusted when the rear lens group frame 33 is fixed is maintained. Even if an external force acts on the imaging element 36 or the second holding frame 35 is deformed by heat, the fixing portion formed by the adhesive 39 is prevented from being deformed or damaged.

According to the endoscope 2 in which the imaging unit 730 is arranged at the distal end portion 6, it is easy to maintain the optical performance even if a load is applied to the holder arranged radially outside the objective lens.

In the first to fourth embodiments and each modified example, both the entire first lens frame and the entire second lens frame are accommodated in the holder. On the other hand, this embodiment is an example showing that part of the first lens frame may protrude outside the holder.

In addition, in each of the above-described embodiments and modifications, the examples in which the members are mainly brought into contact with each other or are fitted with each other have been described when the members are positioned with each other. However, the positioning of the members may be performed by measuring or adjusting the positions of the members by appropriate means.

For example, when fixing members to each other with an adhesive intervening, the positional relationship between the members can be fixed by holding the positions in the axial direction and radial direction while holding the members together with a jig or the like until the curing of the adhesive is completed. In this case, the members may not be in contact with each other. The gap between the members is kept constant even after the adhesive is cured by being filled with the adhesive.

For example, in the first embodiment, when the first front group lens frame 31 and the first holding frame 34 are adhered, the position of the first front group lens frame 31 in the optical axis direction may be adjusted by separating the flange portion 31b from the distal end surface 34c and adhering them together. For example, the same applies when the rear lens group frame 33 and the first holding frame 34 are adhered. Adhesive fixation between other members is similar. The same applies to radial position adjustment in adhesion.

In each of the above embodiments and modifications, the second lens is arranged closer to the image than the first lens, and the second lens frame is arranged closer to the image than the first lens frame. However, the second lens may be arranged closer to the object side than the first lens. In this case, the second lens frame may be arranged closer to the object side than the first lens frame. In this case, the second lens frame and the imaging element are arranged with at least the first lens frame interposed therebetween in the optical axis direction.

In each of the above embodiments and modifications, an example in which the image sensor is held by a holder has been described. However, if the imaging surface of the imaging element can be placed on the image plane of the objective lens, the imaging element need not be held by the holder.

In each of the above embodiments and modifications, an example in which one each of the first lens, the second lens, the first lens frame, the second lens frame, and the holder is provided in the imaging unit has been described. However, in the imaging unit, a plurality of first lenses, second lenses, first lens frames, second lens frames, and holders may be provided.

In the third and fourth embodiments and the third modified example, the outer holding frame 336 constituting the radially outermost portion of the holders of the imaging units 330, 430, and 530 is radially covered by the side surface of the distal end cover 6a of the distal end portion 6 and arranged inside the distal end portion 6. However, the imaging unit holder may form at least part of the side surface of the distal end of the endoscope. That is, the imaging unit holder may include a member that forms at least a portion of the side surface of the distal end cap 6a.

In each of the above embodiments and modifications, an example in which the flange portion has an annular shape when viewed from the axial direction has been described. However, the flange portion need not be continuous in the circumferential direction, and may be provided at a plurality of locations spaced apart in the circumferential direction.

In each of the above-described embodiments and modifications, an example in which the inner peripheral surface and the outer peripheral surface of the cylindrical body are cylindrical surfaces has been described. However, the inner peripheral surface and the outer peripheral surface of the cylindrical body used in the imaging unit are not limited to cylindrical surfaces, as long as the necessary functions such as the function of holding the lens are satisfied. For example, the inner and outer peripheral surfaces may be polygonal when viewed from the axial direction. For example, the inner peripheral surface and the outer peripheral surface may have a surface shape in which appropriate irregularities are formed on a cylindrical surface.

In each of the above embodiments and modifications, an example was explained in which no member other than the first lens frame was arranged between the second lens frame and the holder, and no other member was arranged between the second lens frame and the imaging element.

However, a member other than the first lens frame may be arranged between the second lens frame and the holder as long as the load on the holder can be suppressed from being transmitted to the second lens frame. For example, a member that does not come into contact with either or both of the second lens frame and the holder may be arranged between the second lens frame and the holder. In this case, the second lens frame and the holder do not contact each other and a gap is formed between the second lens frame and the holder, so that the load on the holder can be suppressed from being transmitted to the second lens frame through this member.

Similarly, an appropriate member may be placed between the second lens frame and the imaging element as long as it can suppress the load on the imaging element from being transmitted to the second lens frame. For example, a member that does not come into contact with either or both of the second lens frame and the image sensor may be arranged between the second lens frame and the image sensor. In this case, the second lens frame and the imaging element do not contact each other, and a gap is formed between the second lens frame and the imaging element, so that the load on the imaging element can be suppressed from being transmitted to the second lens frame through this member.

In each of the above embodiments and modifications, when the holder is composed of a plurality of members, the plurality of members are fixed so as not to move relative to each other in the axial direction. However, the plurality of members of the holder may be relatively movable in the axial direction, as long as the relative positions of the lenses held by the holder in the optical axis direction can be determined so that an image can be formed by the objective lens. That is, some members of the holder may be provided movably in the axial direction while being in contact with the holder and other members.

Although preferred embodiments and modifications of the present invention have been described above, the present invention is not limited to such embodiments and modifications. Configuration additions, omissions, substitutions, and other changes are possible without departing from the scope of the present invention.

Also, the present invention is not limited by the above description, but only by the scope of the attached claims.

For example, the imaging units of the first to third embodiments and the first to third modifications may be provided with an objective lens LA instead of the objective lens L.

For example, in the second to fifth embodiments, the first lens frame may be provided with protrusions as in the first modification or the second modification for bonding with the adhesive 39.

According to each of the above-described embodiments, it is possible to provide an endoscope imaging unit and an endoscope that easily maintain optical performance even when a load is applied to the holder arranged radially outside the objective lens.

What is claimed is:

1. An endoscope imaging unit, comprising:
    an objective lens including a first lens and a second lens;
    an imaging element configured to capture an image formed by the objective lens;
    a first lens frame configured to hold the first lens, the first lens frame including a lens barrel that holds the first lens and a flange portion that extends outward from an outer peripheral portion of the lens barrel;
    a second lens frame that is fixed to the first lens frame and holds the second lens; and
    a holder that accommodates both of the first lens frame and the second lens frame therein and holds the outer peripheral surface of the flange portion of the first lens frame,
    wherein a side surface of the flange portion protrudes outward from the first lens frame and is fixed to an inner surface of the holder, and
    the second lens frame is adhesively fixed to the first lens frame within the holder with a gap between the second lens frame and the imaging element and with a gap between the second lens frame and the holder, so that a radial position of the second lens frame can be adjusted.

2. The endoscope imaging unit according to claim 1, wherein the first lens frame is arranged closer to the object-side than the second lens frame.

3. The endoscope imaging unit according to claim 2, wherein
    the first lens frame further includes a protrusion protruding from the flange portion in an axial direction along a central axis of the lens barrel, and
    the second lens frame is fixed to the protrusion with an adhesive at a portion overlapping the protrusion when viewed in a radial direction perpendicular to the axial direction.

4. The endoscope imaging unit according to claim 3, wherein the second lens frame is a lens behind the first lens.

5. An endoscope comprising the endoscope imaging unit according to claim 1.

* * * * *